United States Patent [19]

Schwab et al.

[11] Patent Number: 5,006,515

[45] Date of Patent: Apr. 9, 1991

[54] PHARMACEUTICALS, PHOSPHORUS-CONTAINING 2-ISOXAZOLINES AND ISOXAZOLES CONTAINED THEREIN

[75] Inventors: Wilfried Schwab, Wiesbaden; Robert R. Bartlett, Darmstadt; Ulrich Gebert, Kelkheim; Hans U. Schorlemmer, Marburg; Gerhard Dickneite, Marburg; Hans H. Sedlacek, Marburg, all of Fed. Rep. of Germany

[73] Assignee: Hoechst Aktiengesellschaft, Frankfurt am Main, Fed. Rep. of Germany

[21] Appl. No.: 262,635

[22] Filed: Oct. 26, 1988

[30] Foreign Application Priority Data

Oct. 26, 1987 [DE] Fed. Rep. of Germany ....... 3736113

[51] Int. Cl.$^5$ ..................... A61K 31/675; C07F 9/653
[52] U.S. Cl. ........................ 514/89; 514/92; 514/236.8; 544/137; 546/22; 548/111; 548/119
[58] Field of Search ................ 548/111, 119; 546/22; 544/137; 514/236.8, 89, 92

[56] References Cited

FOREIGN PATENT DOCUMENTS

| | | |
|---|---|---|
| 0087953 | 9/1983 | European Pat. Off. . |
| 0174685 | 2/1986 | European Pat. Off. . |
| 2330685 | 6/1977 | France . |
| 1560711 | 2/1980 | United Kingdom . |
| 1560712 | 2/1980 | United Kingdom . |

OTHER PUBLICATIONS

Schlecker et al., Chemical Abstracts, vol. 96 (1982) 104219b.
Meyer et al., Chemical Abstracts, vol. 103 (1985) 106306q.
A. P. Rakov, et al., Reactions of Aromatic Nitrile Oxides with Some Organophosphorus Compounds, Translated from Zhornal Obsochel Khitnil, vol. 45, No. 12, pp. 2746-2747, Dec. 1975.

Kolokol'tseva et al., C. A., vol. 69, p. 9074, No. 96834y (1968).
Rakov et al., C. A. vol. 84, p. 549, No. 84:59682m (1976).
Franke et al., Synthetsis, pp. 712-714 (1979).
Balthazor et al., J. Org. Chem., 45 pp. 529-532 (1980).

Primary Examiner—Richard L. Raymond
Attorney, Agent, or Firm—Finnegan, Henderson, Farabow, Garrett and Dunner

[57] ABSTRACT

Pharmaceuticals containing or composed of at least one compound of the formula I and/or one of its physiologically tolerated salts where appropriate, where the compounds of the formula I can, where appropriate, be in the form of pure stereoisomers or mixtures thereof; formula I is:

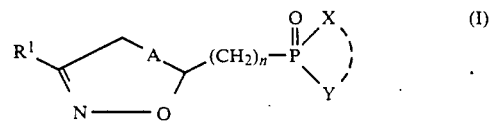

in which
$R^1$ = organic radical or halogen,
A = C,C single or C,C double bond,
n = 0, 1 or 2, and X and Y = alkyl radical or
         = $-OR^2$ or $-NR^2R^3$ with $R^2$ and $R^3$ = H or optionally substituted aliphatic radical.

The pharmaceuticals are suitable for the prophylaxis and/or treatment of diseases of the immune system, especially of tumors, infections and/or autoimmune diseases of the human or animal body and for use as adjuvants for vaccines.

Some of the compounds of the formula I are new; the compounds can be prepared by special processes.

11 Claims, No Drawings

PHARMACEUTICALS, PHOSPHORUS-CONTAINING 2-ISOXAZOLINES AND ISOXAZOLES CONTAINED THEREIN

DESCRIPTION

The present invention relates to new pharmaceuticals which are especially suitable for the prophylaxis and/or treatment of diseases of the immune system in humans and animals, to the pharmacologically active 2-isoxazolines and isoxazoles contained therein, and to processes for the preparation of these heterocyclic compounds serving as active substances.

It is known that the living organism has humoral and cellular immunological defense mechanisms. They serve to neutralize and eliminate foreign bodies which may cause pathogenic changes, mainly microorganisms and neoplastic cells. Immunological investigations have shown that there are connections between the natural decrease, or the decrease provoked by external factors, in immunological activity and the increase in infectious diseases and oncoses. A number of other disorders, such as autoimmune or immune complex diseases, intoxications and septicemias result from loss of control of individual functions of the complex immune system.

This is why there has been for a long time a search for potent and well-tolerated immunomodulators which permit wide therapeutic use for supporting or normalizing the natural defenses of animals and humans.

Attempts to stimulate immunity with BCG (*Bacillus calmette* Guérin) and *Corynebacterium parvum* as well as extracts from Mycobacterium tuberculosis and Brucellae have been unsatisfactory because these substances cause, in the necessary concentrations, serious side effects, for example local granulomas. Furthermore, lack of knowledge of the composition of the heterogeneous mixtures of substances and the structure of the individual components has impeded systematic clinical investigation with readily reproducible results. Hence there is a pressing need for new, well-tolerated immunomodulators which are chemically defined substances.

It has now been found, surprisingly, that the introduction of certain phosphorus-containing radicals, such as a phosphinyl, phosphonyl or phosphono group, into the 5 position of 2-isoxazolines and isoxazoles substituted in the 3 position results in compounds which, by reason of their pharmacological properties, meet the requirements described above and, accordingly, are outstandingly suitable for the prophylaxis and/or treatment of diseases associated with pathological changes in the immune system. While the compounds are extremely well tolerated they have a potent immunomodulating action in mammals, as can be demonstrated, for example, by stimulation of the DTH (delayed-type hypersensitivity) reaction to sheep erythrocytes, activation of mononuclear phagocytes, inhibition of certain aminopeptidases, tumor-inhibiting efficacy, for example against B 16 melanoma in the mouse, and enhancement of the immunological resistance to infections or autoimmune diseases, for example in various experimental models of infection and the model of the active Arthus reaction in the rat and the chronic graft-versus-host (cGvH) model in the mouse. Hence they are valuable active substances which are able to restore the pathologically changed immune system in humans and animals. Although there have already been descriptions in the literature of the synthesis of some 2-isoxazolin-5-yl- and 2-isoxazolin-5-yl-methyl-phosphonates (Zh. Obshch. Khim. 38 (1968), 1248–1254; Zh. Obshch. Khim. 45 (1975), 2746–2747), isoxazol-5-ylmethyl-phosphonates (Synthesis 1979, 712–714) and 5-methylmethoxyphosphinylisoxazoles (J. Org. Chem. 45 (1980), 529–531), nothing has yet been disclosed about pharmacological properties of these compounds which would suggest their use as active substances in pharmaceuticals. The diethyl 3-(2-nitro-5-(2-chloro-4-trifluoromethylphenoxy)phenyl)-2-isoxazolin-5-ylphosphonate which is mentioned in the Patent EP 174,685 and alleged to have herbicidal effects is, at the most, a potential plant-protection agent.

In contrast, the present invention describes 3-substituted 2-isoxazolines and isoxazoles having a phosphorus-containing radical in the 5 position, most of which are new and which, by reason of their abovementioned immunomodulating properties, are suitable as active substances in pharmaceuticals for the prophylaxis and/or treatment of tumors, infections and autoimmune diseases.

Hence the invention relates to pharmaceuticals which contain as active substances phosphorus-containing 2-isoxazolines or isoxazoles of the general formula I and/or, where appropriate, the physiologically tolerated salts thereof,

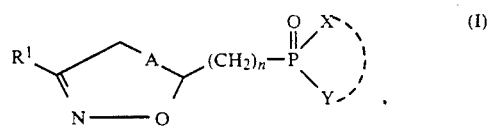

where
$R^1$ represents
  (a) a straight-chain or branched alkyl or alkenyl group which has 1 to 6 carbon atoms and whose carbon chain can be substituted by halogen, for example fluorine, chlorine or bromine, hydroxyl, $(C_1-C_4)$alkoxy, $(C_1-C_4)$acyloxy or aryl which is optionally substituted by $(C_1-C_4)$alkoxy or halogen, or
  (b) a mono- or binuclear aromatic or heteroaromatic group having 1 or 2 nitrogen atoms and/or one sulfur or oxygen atom in the ring system, it being possible for this group to be substituted one or more times and identically or differently by straight-chain or branched $(C_1-C_4)$alkyl, $(C_3-C_6)$cycloalkyl, hydroxyl, $(C_1-C_3)$alkoxy, aryloxy, $(C_1-C_4)$acyloxy or benzoyloxy, halogen, trifluoromethyl, nitro, optionally mono- or disubstituted amino, $(C_1-C_4)$-alkoxycarbonyl, carboxyl, carbamoyl, $(C_1-C_4)$alkylcarbonyl, whose carbonyl group can in each case also be in ketalized form, or benzyl or phenyl which is optionally ring-substituted by $(C_1-C_4)$alkyl, halogen or $(C_1-C_3)$alkoxy, or
  (c) carboxyl or alkoxycarbonyl having 1 to 4 carbon atoms in the alkyl moiety or
  (d) arylcarbonyl which is optionally substituted in the aryl moiety by $(C_1-C_4)$alkyl, halogen or $(C_1-C_3)$alkoxy, or
  (e) halogen, preferably chlorine or bromine,
A denotes a C,C single bond or a C,C double bond,
n denotes an integer from 0 to 2, and
X and Y, which can be identical or different, each denote, independently of one another, a straight-chain or branched $(C_1-C_4)$alkyl group, the radical $-OR^2$ or the group $-NR^2R^3$, where $R^2$ and $R^3$ represent hydrogen or optionally substituted ($C_1$-$C_6$)alkyl radicals which, in the group —$NR^2R^3$, can also form together with the nitrogen atom a five- to seven-membered ring or, in the structural element —P(O)($OR^2$)$_2$, can form together with the phosphorus atom a heterocycle of the formula

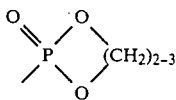

which is optionally also substituted by ($C_1$-$C_3$)alkyl, ($C_1$-$C_4$)alkoxycarbonyl or carboxyl,
and where the compounds of the formula I can, where appropriate, be in the form of pure stereoisomers or mixtures thereof.

The preferred pharmaceuticals in this connection are those which contain compounds of the formula I and/or, where appropriate, salts thereof, in which
$R^1$ represents
(a) optionally branched ($C_1$-$C_4$)alkyl or ($C_1$-$C_4$)hydroxyalkyl such as methyl, ethyl, propyl, isopropyl, butyl, tert.butyl, hydroxymethyl or 1-hydroxy-1-methylethyl, or phenyl($C_1$-$C_2$)alkyl or phenyl($C_2$-$C_3$)alkenyl such as benzyl or styryl,
(b) phenyl, naphthyl, pyridyl or thienyl, each of which is unsubstituted or substituted one or more times by ($C_1$-$C_4$)alkyl, such as methyl, ethyl or tert.butyl, hydroxyl, ($C_1$-$C_2$)alkoxy, phenoxy, halogen such as chlorine or fluorine, trifluoromethyl, nitro, di($C_1$-$C_2$)alkylamino such as dimethyl- or diethylamino, ($C_1$-$C_2$)alkoxycarbonyl such as meth- or ethoxycarbonyl, carboxyl or phenyl,
(c) carboxyl or meth- or ethoxycarbonyl,
(d) benzoyl,
(e) chlorine or bromine,
A denotes a C,C single bond or a C,C double bond, n represents 0 or 1, and
X and Y, which can be identical or different, represent independently of one another a methyl or ethyl group or the radicals —$OR^2$ or —$NR^2R^3$, where $R^2$ represents hydrogen, methyl or ethyl, and $R^3$ likewise represents hydrogen, methyl or ethyl, or else represent the carbon skeleton of an optionally carboxyl-protected amino acid, the radicals $R^2$ and $R^3$ in the group —$NR^2R^3$ can also form together with the nitrogen atom a pyrrolidine, piperidine or morpholine ring, and the radicals —$OR^2$ in the structural element—P(O)($OR^2$)$_2$ can form together with the phosphorus atom a 2-oxo-1,3,2-dioxapholane or 2-oxo-1,3,2-dioxaphosphorinane ring, each of which is optionally substituted by ($C_1$-$C_2$)alkyl, and where these compounds can, if appropriate, be in the form of pure stereoisomers or mixtures thereof.

The pharmaceuticals amongst these which are in turn preferred are those which contain compounds of the formula I and/or, where appropriate, salts thereof, in which either $R^1$ represents tert.butyl, benzyl, phenyl, naphthyl, pyridyl or thienyl, or phenyl which is substituted by methyl, hydroxyl, methoxy, phenoxy, chlorine, fluorine, trifluoromethyl, nitro, dimethylamino, methoxycarbonyl or carboxyl, or X and Y denote, independently of one another, hydroxyl, methoxy or ethoxy, or X denotes methyl and Y denotes hydroxyl, methoxy or ethoxy, and where these compounds can, where appropriate, be in the form of pure stereoisomers or mixtures thereof.

Furthermore, the pharmaceuticals amongst these to be emphasized are those which contain compounds of the formula I and/or, where appropriate, salts thereof in which $R^1$, X and Y all have the abovementioned meanings, especially when, furthermore, A represents a C,C single bond, and n has the value 0, where these compounds can, where appropriate, be in the form of pure stereoisomers or mixtures thereof.

Finally, a particularly preferred group of pharmaceuticals is represented by those which contain compounds of the formula I and/or salts thereof in which $R^1$ represents tert.butyl or phenyl, X and Y each denote hydroxyl, or X denotes methyl and Y denotes hydroxyl, A represents a C,C single bond, and n has the value 0, for example 3-phenyl-2-isoxazolin-5-ylphosphonic acid, 3-phenyl(or 3-tert.butyl)-2-isoxazolin-5-yl(P-methyl)-phosphinic acid, where these compounds can be in the form of pure stereoisomers or mixtures thereof.

The invention also relates to the use of the pharmaceuticals according to the invention for the prophylaxis and/or treatment of diseases of the immune system in humans and animals, especially of tumors, infections and/or autoimmune diseases.

The invention furthermore relates to new phosphorus-containing 2-isoxazolines and isoxazoles of the general formula I, to their stereoisomeric forms where appropriate, and to their physiologically tolerated salts where appropriate, where
$R^1$ represents
(a) a straight-chain or branched alkyl or alkenyl group which has 1 to 6 carbon atoms and whose carbon chain can be substituted by halogen, for example fluorine, chlorine or bromine, hydroxyl, ($C_1$-$C_4$)alkoxy, ($C_1$-$C_4$)acyloxy or aryl which is optionally substituted by ($C_1$-$C_4$)alkoxy or halogen, or
(b) a mono- or binuclear aromatic or heteroaromatic group having 1 or 2 nitrogen atoms and/or one sulfur or oxygen atom in the ring system, it being possible for this group to be substituted one or more times and identically or differently by straight-chain or branched ($C_1$-$C_4$)alkyl, ($C_3$-$C_6$)cycloalkyl, hydroxyl, ($C_1$-$C_3$)alkoxy, aryloxy, ($C_1$-$C_4$)acyloxy or benzoyloxy, halogen, trifluoromethyl, nitro, optionally mono- or disubstituted amino, ($C_1$-$C_4$)alkoxycarbonyl, carboxyl, carbamoyl, ($C_1$-$C_4$)alkylcarbonyl, whose carbonyl group can in each case also be in ketalized form, or benzyl or phenyl which is optionally ring-substituted by ($C_1$-$C_4$)alkyl, halogen or ($C_1$-$C_3$)alkoxy, or
(c) carboxyl or alkoxycarbonyl having 1 to 4 carbon atoms in the alkyl moiety or
(d) arylcarbonyl which is optionally substituted in the aryl moiety by ($C_1$-$C_4$)alkyl, halogen or ($C_1$-$C_3$)alkoxy, or
(e) halogen, preferably chlorine or bromine,
A denotes a C,C single bond or a C,C double bond, n denotes an integer from 0 to 2, and
X and Y, which can identical or different, each denote, independently of one another, a straight-chain or branched ($C_1$-$C_4$)alkyl group, the radical —$OR^2$ or the group —$NR^2R^3$, where $R^2$ and $R^3$ represent hydrogen or optionally substituted ($C_1$-$C_6$)alkyl radicals which, in the group —$NR^2R^3$, can also form together with the nitrogen atom a five- to seven-membered ring or, in the structural element —P(O)($OR^2$)$_2$, can form together with the phosphorus atom a heterocycle of the formula

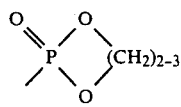

which is optionally also substituted by $(C_1-C_3)$alkyl, $(C_1-C_4)$alkoxycarbonyl or carboxyl, with the exception of the compounds 3-phenyl-2-isoxazolin-5-ylphosphonic acid, dimethyl 3-methyl(and phenyl)-2-isoxazolin-5-ylphosphonate, dipropyl 3-(3-nitrophenyl)-2-isoxazolin-5-ylphosphonate, diethyl 3-(2-nitro-5-(2-chloro-4-trifluoromethylphenoxy)phenyl)-2-isoxazolin-5-ylphosphonate, 3-methyl(and phenyl)-2-isoxazolin-5-ylphosphonic tetramethyldiamide, 3-phenyl-2-isoxazolin-5-ylmethylphosphonic acid and the diethyl ester thereof, diethyl 3-methyl(ethyl, isopropyl, tert.butyl, methoxymethyl, phenyl and ethoxycarbonyl)-5-isoxazolylmethylphosphonate, 3-(4-fluoro- and 4-chlorophenyl)-5-isoxazolyl(P-methyl)phosphinic acid and methyl 3-phenyl-5-isoxazolyl(P-methyl)phosphinate, where the racemic forms are being dealt with where appropriate.

Preferred in this connection are those compounds of the formula I, including their stereoisomeric forms where appropriate and their salts where appropriate, in which $R^1$ represents (a) optionally branched $(C_1-C_4)$alkyl or $(C_1-C_4)$hydroxyalkyl such as methyl, ethyl, propyl, isopropyl, butyl, tert.butyl, hydroxymethyl or 1-hydroxy-1-methylethyl, or phenyl$(C_1-C_2)$alkyl or phenyl($C_2-C_3$)alkenyl such as benzyl or styryl, (b) phenyl, naphthyl, pyridyl or thienyl, each of which is unsubstituted or substituted one or more times by $(C_1-C_4)$alkyl such as methyl, ethyl or tert.butyl, hydroxyl, $(C_1-C_2)$alkoxy, phenoxy, halogen such as chlorine or fluorine, trifluoromethyl, nitro, di$(C_1-C_2)$alkylamino such as dimethyl- or diethylamino, $(C_1-C_2)$alkoxycarbonyl such as meth- or ethoxycarbonyl, carboxyl or phenyl, (c) carboxyl or meth- or ethoxycarbonyl, (d) benzoyl, (e) chlorine or bromine, A denotes a C,C single bond or a C,C double bond, n represents 0 or 1, and X and Y, which can be identical or different, represent independently of one another a methyl or ethyl group or the radicals $-OR^2$ or $-NR^2R^3$, where $R^2$ represents hydrogen, methyl or ethyl, and $R^3$ likewise represents hydrogen, methyl or ethyl, or else represent the carbon skeleton of an optionally carboxyl-protected amino acid, the radicals $R^2$ and $R^3$ in the group $-NR^2R^3$ can also form together with the nitrogen atom a pyrrolidine, piperidine or morpholine ring, and the radicals $-OR^2$ in the structural element $-P(O)(OR^2)_2$ can form together with the phosphorus atom a 2-oxo-1,3,2-dioxaphospholane or 2-oxo-1,3,2-dioxaphosphorinane ring, each of which is optionally substituted by $(C_1-C_2)$alkyl, with the exception of the compounds 3-phenyl-2-isoxazolin-5-ylphosphonic acid, dimethyl 3-methyl(and phenyl)-2-isoxazolin-5-ylphosphonate, 3-methyl-(and phenyl)-2-isoxazolin-5-ylphosphonic tetramethyldiamide, 3-phenyl-2-isoxazolin-5-ylmethylphosphonic acid and the diethyl ester thereof, diethyl 3-methyl(ethyl, isopropyl, tert.butyl, phenyl and ethoxycarbonyl)-5-isoxazolylmethylphosphonate, 3-(4-fluoro- and 4-chloro-phenyl)-5-isoxazolyl(P-methyl)-phosphinic acid and methyl 3-phenyl-5-isoxazolyl(P-methyl)phosphinate, where the racemic forms are being dealt with where appropriate.

The compounds amongst those which are in turn preferred are those in which either $R^1$ represents tert.butyl, benzyl, phenyl, naphthyl, pyridyl or thienyl, or phenyl which is substituted by methyl, hydroxyl, methoxy, phenoxy, chlorine, fluorine, trifluoromethyl, nitro, dimethylamino, methoxycarbonyl or carboxyl, or X and Y denote, independently of one another, hydroxyl, methoxy or ethoxy, with the exception of the compounds 3-phenyl-2-isoxazolin-5-ylphosphonic acid, dimethyl 3-methyl(and phenyl)-2-isoxazolin-5-ylphosphonate, 3-methyl-(and phenyl)-2-isoxazolin-5-ylphosphonic tetramethyldiamide, 3-phenyl-2-isoxazolin-5-ylmethylphosphonic acid and the diethyl ester thereof, diethyl 3-methyl(ethyl, isopropyl, tert.butyl, phenyl and ethoxycarbonyl)-5-isoxazolylmethylphosphonate, 3-(4-fluoro- and 4-chloro-phenyl)-5-isoxazolyl(P-methyl)-phosphinic acid and methyl 3-phenyl- 5-isoxazolyl(P-methyl)phosphinate, where the racemic forms are being dealt with where appropriate.

Furthermore, the compounds, including their stereoisomeric forms where appropriate, and their salts where appropriate, which are to be emphasized are those in which $R^1$, X and Y all have the abovementioned meanings, especially when, furthermore, A represents a C,C single bond, and n has the value 0, with the exception of the compounds 3-phenyl-2-isoxazolin-5-ylphosphonic acid and the dimethyl ester thereof, 3-phenyl-2-isoxazolin-5-ylmethylphosphonic acid and the diethyl ester thereof, diethyl 3-tert.butyl(and phenyl)-5-isoxazolylmethylphosphonate, 3-(4-fluoro- and 4-chlorophenyl)-5-isoxazolyl(P-methyl)phosphinic acid and methyl 3-phenyl-5-isoxazolyl(P-methyl)phosphinate, where the racemic forms thereof are being dealt with where appropriate.

Finally, a particularly preferred group of compounds, including their stereoisomeric forms and their salts, are represented by those in which $R^1$ represents tert.butyl or phenyl, X and Y each denote hydroxyl, or X denotes methyl and Y denotes hydroxyl, A represents a C,C single bond, and n has the value 0, for example 3-phenyl-2-isoxazolin-5-ylphosphonic acid or 3-phenyl(or 3-tert.butyl)-2-isoxazolin-5-yl(P-methyl)phosphinic acid, with the exception of racemic 3-phenyl-2-isoxazolin-5-ylphosphonic acid.

The invention also relates to a process for the preparation of the phosphorus-containing 2-isoxazolines and isoxazoles of the general formula I, their stereoisomeric forms where appropriate, and their physiologically tolerated salts where appropriate, which comprises reacting a nitrile oxide of the formula II $$R^1C\equiv N\rightarrow O \qquad (II)$$

(a) in the case where A in formula I denotes a C,C single bond, with an olefinic phosphorus compound of the formula III

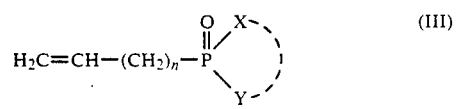

or (b) in the case where A in the formula I denotes a C,C double bond, with an olefinic phosphorus compound of the formula IV

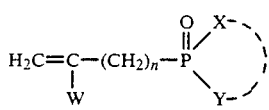

(IV)

to give a 2-isoxazoline of the formula V

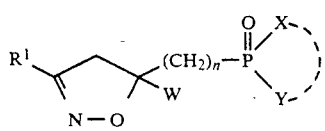

(V)

and eliminating HW from this intermediate under basic conditions or by exposure to heat, where $R^1$, n, X and Y in formulae II to V have the abovementioned meanings, and W represents a leaving group such as halogen, preferably bromine or chlorine, a $(C_1-C_6)$alkoxy or sulfonate group, and, where appropriate, (c) cleaving a phosphonic or phosphinic ester of the formula I obtained as in (a) or (b) to give the phosphonic monoester or to give the phosphonic or phosphinic acid of the formula I, or (d) reacting a dialkyl phosphonate of the formula I obtained as in (a) or (b) with an amine of the formula $HNR^2R^3$ (VI) with replacement of one of the two alkoxy groups on the phosphorus by the radical $-NR^2R^3$ to give a monoester monoamide of the formula I, where $R^2$ and $R^3$ have the abovementioned meanings, and compounds in which $R^1$ denotes halogen are excepted, or (e) initially converting a phosphonic acid of the formula I prepared as in (a), (b) or (c) into an acid derivative activated on the phosphorus atom, and subsequently reacting the latter with alcohols of the formula $R^2OH$ (VII) or a diol of the formula $HO-(CH_2)_{2-3}-OH$ (VIII) and/or amines of the formula VI, as selected, to give a mono- or optionally mixed diester, a cyclic ester, a monoester monoamide or a mono- or optionally mixed diamide of the formula I, or reacting a phosphonic monoester of the formula I obtained as in (a), (b) or (c), after activation on the phosphorus atom, with an alcohol VII or an amine VI to give an optionally mixed diester or a monoester monoamide of the formula I, or reacting a phosphinic acid of the formula I prepared as in (a), (b) or (c), after activation on the phosphorus atom, with an alcohol VII or an amine VI to give an ester or amide of the formula I, where $R^1$ and $R^3$ in formula VI have the abovementioned meanings, $R^2$ in formula VII represents optionally substituted $(C_1-C_6)$alkyl, and the alkylene chain $-(CH_2)_{2-3}-$ in formula VIII can also be substituted by $(C_1-C_3)$alkyl, $(C_1-C_4)$alkoxycarbonyl or carboxyl, or (f) reacting a 3-chloro(or bromo)-2-isoxazoline-phosphonic di- or monoester or -phosphinic ester of the formula I which has been prepared as in (a) and in which n denotes an integer from 0 to 2, with tri(C$_1$-C$_4$)alkylhalogenosilanes to give, with ester cleavage and simultaneous replacement of chlorine or bromine by the halogen atom of the particular silane used, the corresponding 3-halogeno-2-isoxazoline-phosphonic or -phosphinic acids of the formula I, or (g) resolving a compound of the formula I which has been obtained as in (a) to (f), and which, by reason of its chemical structure, occurs in diastereomeric or enantiomeric forms, into the pure stereoisomers in a manner known per se, with the compounds of the formula I prepared as in (a) to (g) being either isolated in free form or, where appropriate, converted into physiologically tolerated salts.

Physiologically tolerated salts are prepared from compounds of the formula I which are able to form salts, including the stereoisomeric forms thereof where appropriate, in a manner known per se. Thus, the phosphonic and phosphinic acids and the phosphonic monoesters form with basic reagents, such as hydroxides, alcoholates, carbonates, bicarbonates, ammonia or organic bases, for example trimethyl- or triethylamine, ethanolamine or else basic amino acids, for example lysine, ornithine or arginine, stable alkali metal, for example sodium or potassium, alkaline earth metal, such as calcium or magnesium, or optionally substituted ammonium, salts, it also being possible in the case of the phosphonic acids to obtain stable hydrogen phosphonates by conversion of only one of the two acidic OH groups into the salt form. Where the compounds of the formula I have a basic group in the radical $R^1$ it is also possible with strong acids to prepare stable non-toxic acid addition salts. Suitable for this purpose are both inorganic and organic acids, such as hydrochloric, hydrobromic, sulfuric, phosphoric, methanesulfonic, benzenesulfonic, p-toluenesulfonic, 4-bromobenzenesulfonic, cyclohexylamidosulfonic or trifluoromethanesulfonic acid.

The nitrile oxides of the formula II which are used as starting materials in the 1,3-dipolar cycloaddition onto the olefins III and IV by process variants (a) and (b) are mostly known or can be prepared by methods known from the literature. Thus, for example, they can be prepared by dehydration of aliphatic or araliphatic nitro compounds, advantageously with isocyanates such as phenyl isocyanate or 1,4-diisocyanatobenzene by the method of Mukaiyama (J. Am. Chem. Soc. 82 (1960), 5339-5342) or, starting from hydroxamoyl halides, which themselves can be obtained by methods which are likewise known from the literature, for example by halogenation of aldoximes (K. C. Liu et al., J. Org. Chem. 45 (1980), 3916-3918; C. J. Peake et al., Synth. Commun. 16 (1986), 763-765; D. M. Vyas et al., Tetrahedron Lett. 25(1984), 487-490), by base-catalyzed dehydrohalogenation, preferably by the "in situ" process developed by Huisgen (Chem. Ber. 106 (1973), 3258-3274).

The olefinic phosphorus compounds of the formulae III and IV which additionally serve as reactants are likewise mostly known from the literature or can even be bought, such as, for example, diethyl vinylphosphonate, or else can easily prepared by processes described in the literature (H. J. Kleiner et al., Angew. Chem. 94 (1982), 561-562; T. Ya. Medved et al., Zh. Akad. Nauk. SSSR, Ser. Khim, 1956, 684; German Offenlegungsschrift 2,601,467). Suitable compounds of the formula IV are mainly those in which the leaving group W denotes methoxy or ethoxy, alkanesulfonyloxy, for example methane- or trifluoromethanesulfonyloxy, or arenesulfonyloxy such as, for example, benzene-, p-toluene- or 4-bromobenzenesulfonyloxy, but preferably denotes halogen, especially bromine or chlorine.

As a rule, the generation of the nitrile oxides II, either from the nitro compounds by the Mukaiyama method or else from the hydroxamoyl halides by the Huisgen method, and the 1,3-dipolar cycloaddition thereof onto the olefinic phosphorus compounds III and IV which, in the case of the phosphonic and phosphinic acids, are advantageously employed in the form of the esters, for example the methyl or ethyl ester, are carried out in a so-called one-pot reaction without isolation of the particular intermediates, it being advisable to use an aprotic solvent or diluent which is inert toward the reactants. Examples suitable for this purpose are ethyl acetate, dimethylformamide, dimethylacetamide, dimethyl sulfoxide, ethers such as diisopropyl ether, diethyl ether, tert.butyl methyl ether and tetrahydrofuran, halogenated hydrocarbons such as dichloromethane or chloroform, hydrocarbons such as hexane, cyclohexane, benzene and toluene, and other substituted aromatic hydrocarbons, as well as mixtures of the said solvents, but preferably the aliphatic ethers or aromatic hydrocarbons. It is also possible in the Huisgen hydroxamoyl halide method to carry out the cycloaddition, when inorganic bases are used to generate the nitrile oxide, additionally in two-phase solvent mixtures, for example ethyl acetate/water or dichloromethane/water. On the other hand, when organic bases are used for the dehydrohalogenation it is preferable to employ the abovementioned chlorinated hydrocarbons or aliphatic ethers. The preparation of the nitrile oxides and the cycloaddition are, as a rule, carried out at temperatures between $-20°$ C. and $+50°$ C., but preferably between $0°$ and $+40°$ C.

It is likewise unnecessary to isolate the isoxazolines V in the base-catalyzed conversion of the intermediates V into the isoxazoles of the formula I with elimination of HW, on the contrary it is possible and advantageous for the intermediates to be converted directly into the isoxazoles by use of the base which is utilized for the nitrile oxide synthesis in an excess of up to 5-fold, but preferably of two-fold. Examples of bases suitable for this purpose are sodium or potassium hydroxide or carbonate as well as organic amines such as mono-, di- or trialkylamines, but preferably trialkylamines such as, for example, trimethyl- or triethylamine. However, it is also possible in general to convert the isoxazolines V into the isoxazoles of the formula I by thermal elimination at temperatures above 50° C.

The ester cleavage of the phosphonic and phosphinic esters of the formula I to give the corresponding phosphonic monoesters or phosphonic or phosphinic acids of the formula I by procedure (c) is carried out by standard processes known to those skilled in the art, using acidic or alkaline reagents. Thus, the reaction can be carried out both with inorganic and organic acids or bases in aqueous solution or protic organic solvents. It is also possible to use trialkylsilyl halides in aprotic solvents.

The conversion of the phosphonic diesters into the corresponding phosphonic acids takes place advantageously under acidic conditions. It proves particularly suitable to operate in anhydrous medium with hydrogen halides such as hydrogen chloride, bromide or iodide, in organic carboxylic acids, for example formic or acetic acid, with the system composed of hydrogen bromide and glacial acetic acid being in turn preferred. The reaction is carried out with a 0.5 to 4 normal, preferably with a 2 to 4 normal, HBr/glacial acetic acid solution at temperatures between 0° C. and 100° C., but preferably between 20° and 50° C. To prepare the phosphonic monoesters, the phosphonic diesters are as a rule subjected to alkaline hydrolysis, preferably in aqueous medium. This entails the use of, advantageously, an organic solvent which is miscible with water to dissolve the diester, for example a lower alcohol such as methanol or ethanol, and then addition of a 0.1 to 5 normal, but preferably 0.5 to 2 normal, aqueous base, for example sodium or potassium hydroxide. The base can be employed in stoichiometric amounts or in an excess of up to 10-fold, preferably 2- to 4-fold. The reaction is carried out at temperatures between 0° C. and the boiling point of the reaction medium used. A temperature range from 0° to 50° C. is preferred, especially from 20° to 40° C. Both the procedures described above for ester cleavage are equally suitable for the preparation of the phosphinic acids from the corresponding phosphinic esters. The phosphonic acids, phosphonic monoesters and phosphinic acids can, as a rule, be isolated as crystalline products, some of which may form stable hydrates on recrystallization from water or solvent mixtures containing water.

The aminolysis of phosphonic diesters of the formula I with the primary or secondary amines of the formula VI to give the corresponding phosphonic monoester monoamides of the formula I by procedure (d) can be carried out either without diluent or in protic and aprotic solvents at, as a rule, elevated temperatures. Suitable and preferred amines VI are lower mono- or, especially, dialkylamines, for example methyl- and ethylamine or dimethyl- and diethylamine, as well as cyclic amines such as pyrrolidine, piperidine and morpholine. Suitable solvents are, inter alia, halogenated hydrocarbons, ethers, aromatic hydrocarbons and alcohols, preferably lower alcohols such as methanol and ethanol, as well as cyclic ethers, for example dioxane. The particular amine VI is employed in an excess of 2- to 100-fold, advantageously 5- to 10-fold. The reaction temperature is usually chosen in the range between 40° and 100° C., preferably 60° and 80° C.

It is advantageous to use for the ester and/or amide formation from the phosphonic acids, phosphonic monoesters and phosphinic acids of the formula I by procedure (e) the acid derivatives activated on the phosphorus atom. It is possible to use for the activation of the (P-OH) groups the reagents known from nucleotide chemistry, for example 1-mesitylsulfonyl-3-nitro-1H-1,2,4-triazole and mesitylsulfonyl chloride together with tetrazole or—in a more straightforward variant—phosphorus halides such as phosphorus trihalides, preferably phosphorus trichloride in this case, as well as phosphorus oxychloride and phosphorus pentahalides, preferably phosphorus pentachloride in this case. The acid derivatives having two reactive groups obtained from the phosphonic acids of the formula I in this way can be reacted, by standard processes sufficiently known to those skilled in the art, with one equivalent of alcohol of the formula VII, preferably in the form of an alkali metal or alkaline earth metal alcoholate, to give monoesters of the formula I, with at least two equivalents of alcohol VII to give diesters of the formula I, successively with one equivalent of each of two different alcohols VII to give mixed diesters of the formula I, with one equivalent of diol VIII to give cyclic esters of the formula I, successively with one equivalent of each of alcohol VII and amine VI to give monoester monoamides of the formula I, with one equivalent of amine VI to give monoamides of the formula I, with at least two equivalents of amine VI to give diamides of the formula I or, successively with one equivalent of each of two different amines VI to give mixed diamides of the formula I. Obtained analogously from the phosphonic monoesters of the formula I, after activation of the free (P—OH) group, are optionally mixed diesters of the formula I by reaction with one equivalent of alcohol VII, or monoester monoamides of the formula I with one equivalent of amine VI. Likewise, the phosphinic acids react, after activation of the (P-OH) group, with one equivalent of alcohol VII or amine VI to give the corresponding phosphinic esters or amides of the formula I.

It is also possible in this way particularly advantageously to prepare the P-alkoxy- and P-alkylphosphapeptides, which are generally known to be labile, when amino acids are employed as amine component VI, mainly neutral amino acids such as glycine, alanine, valine, leucine or isoleucine, expediently in carboxyl-protected form, for example as benzyl or tert.butyl esters. If the (P-OH) groups are activated with phosphorus-halogen compounds, then the reaction to form the amide bond is advantageously carried out with at least twice the stoichiometric amount of the particular amine VI or else in the presence of a second base which is employed in at least stoichiometric amount, preferably of a tertiary amine such as triethylamine, morpholine or even pyridine, in order to bind the hydrogen halide which is liberated. When arenesulfonyl compounds are used as activating reagents, mainly used as reaction medium are dipolar aprotic solvents such as dioxane, pyridine or dimethylformamide. On the other hand, if activation is carried out with phosphorus halides, then also suitable are aromatic and halogenated hydrocarbons. The temperatures for this reaction are, as a rule, between $-20°$ and $+40°$ C., but preferably between $0°$ and $20°$ C.

The replacement of halogen in the 3-chloro(or bromo)-2-isoxazoline-phosphonic or -phosphinic esters of the formula I with trialkylhalogenosilanes with simultaneous ester cleavage by procedure (f) is expediently carried out in a dipolar aprotic solvent at temperatures between about $0°$ C. and the boiling point of the particular reaction medium used. It is particularly suitable to use halogenated hydrocarbons such as, for example, dichloromethane. Suitable trialkylhalogenosilanes are represented, for example, by trimethylchloro- and trimethylbromosilane.

The separation of those compounds of the formula I which, by reason of their chemical structure, occur in diastereomeric or enantiomeric forms, and are produced in the synthesis as mixtures thereof, into the pure stereoisomers by procedure (g) is carried out either by chromatography on a support material which is chiral where appropriate or, where the racemic compounds of the formula I are able to form salts, by fractional crystallization of the diastereomeric salts formed with an optically active base or acid as auxiliary. However, stereospecific synthesis of compounds of the formula I is also possible in principle if, in process variants (b) to (f), the relevant starting materials are employed for the synthesis in the form of pure stereoisomers. This very particularly applies to the preparation of phosphapeptides by reaction of the activated acid derivatives of phosphonic acids, phosphonic monoesters and phosphinic acids of the formula I with amino acids by procedure (e). Examples of suitable chiral stationary phases for the resolution, by thin-layer or column chromatography, of racemates, especially including the 2-isoxazolines having an asymmetric carbon atom in ring position 5, which are as a rule produced as racemates by process variant (a), are modified silica gel supports (called Pirkle phases) and high molecular weight carbohydrates such as cellulose, tribenzoylcellulose and—especially for resolutions on a relatively large preparative scale—triacetylcellulose. These optically active support materials are commercially available. The mobile phases used are those solvents or solvent mixtures which are unable to undergo reaction with the functional groups of the stereoisomeric compounds which are to be separated. In order to separate the enantiomers, for example of the racemic phosphonic acids, the acidic monoesters thereof and phosphinic acids of the formula I, by fractional crystallization, a procedure known to those skilled in the art, using an optically active base, is used to form the two diastereoisomeric salts, which differ in solubility, and the less soluble component is separated off as solid, the more soluble diastereoisomer is isolated from the mother liquor, and the pure diastereomers obtained in this way are decomposed to the desired enantiomers. Readily obtainable optically active bases which may be mentioned as preferred are amine bases for example $(-)$-nicotine, $(-)$-brucine, $(+)$- and $(-)$-1-phenylethylamine, $(-)$-norephedrine, $(+)$-norpseudoephedrine, $(+)$-3-aminomethylpinane, $(-)$-quinine, $(+)$-quinidine, $(-)$-cinchonidine, $(+)$-cinchonine, L-lysine and L- or D-arginine.

The phosphonic and phosphinic acids and the acidic phosphonic monoesters of the formula I also form stable salts with quaternary organic bases, for example with commercially available high molecular anion exchangers in the hydroxide form, such as, for example Amberlite ®IRA 402 or the liquid ion exchanger Amberlite ® LA-2. Use can advantageously be made of this property in the purification of the crude acids obtained, by extracting them from aqueous solution with Amberlite ® LA-2 dissolved in an organic solvent of low miscibility with water, such as toluene, cyclohexane or ethyl acetate. The acids are expediently detached from the exchanger resin with strong aqueous bases in excess, primarily with 1 to 25% strength, but preferably 5 to 15% strength, aqueous ammonia solution. The pure ammonium salts produced thereby can be crystallized as such or else converted into the free acids in alcoholic, preferably methanolic, or aqueous, solution with acids or acidic ion exchangers, for example Amberlyst ®15. This straightforward purification process has distinct advantages over conventional methods of purification by crystallization or chromatography.

The pharmaceuticals according to the invention, which contain as active substances the compounds of the formula I, where appropriate in the form of pure stereoisomers and/or as physiologically tolerated salts, either alone, for example in microcapsules, in mixtures with one another or, preferably, in combination with suitable pharmaceutical excipients, diluents and/or other auxiliaries, can be administered parenterally, rectally or orally.

Examples of suitable solid or liquid pharmaceutical forms are granules, powders, coated tablets, tablets, (micro)capsules, suppositories, syrups, elixirs, suspensions, emulsions, drops or injectable solutions, as well as products with protracted release of active substance, for the preparation of which it is normal to use auxiliaries such as excipients, disintegrants, binders, coating agents, swelling agents, glidants or lubricants, flavorings, sweeteners or solubilizers. Examples of auxiliaries which are often used and may mentioned are magnesium carbonate, titanium dioxide, lactose, mannitol and other sugars, talc, lactalbumin, gelatin, starch, cellulose and derivatives thereof, animal and vegetable oils, such as fish liver oil, sunflower, peanut or sesame oil, polyethylene glycols and solvents such as, for example, sterile water, physiological saline and monohydric or polyhydric alcohols, for example glycerol. For the preparation of aqueous solutions of the phosphonic and phosphinic acids, as well as the phosphonic monoesters, of the formula I, which have a strongly acidic reaction, the formulation of the active substance is expediently such that it is in the form of a salt with a physiologically tolerated pH.

The pharmaceutical products are preferably prepared and administered in dosage units, each unit containing as active ingredient a defined dose of at least one compound of the formula I, where appropriate in the form of a pure stereoisomer and/or salt. In the case of solid dosage units such as tablets, capsules, coated tablets or suppositories, this dose can be up to about 1000 mg, but preferably about 50 to 300 mg, and in the case of injection solutions in ampule form it can be up to about 300 mg, but preferably about 10 to 100 mg.

Daily doses indicated for the treatment of an adult patient weighing about 70 kg are—depending on the efficacy of the compounds of the formula I, where appropriate in the form of pure stereoisomers and/or salts, in humans and animals—about 50 to 3000 mg of active substance, preferably about 150 to 1000 mg, on oral administration, and about 50 to 1000 mg, preferably about 100 to 300 mg, on intravenous administration. However, in certain circumstances higher or lower daily doses may also be appropriate. The daily dose may be administered both by a single administration in the form of a single dosage unit or else several smaller dosage units, and by multiple administration of divided doses at defined intervals.

Finally, in the preparation of the abovementioned pharmaceutical forms, the compounds of the formula I, their stereoisomeric forms where appropriate and/or their physiologically tolerated salts where appropriate can also be formulated together with other suitable active substances, for example antibacterial, antimycotic, antiviral or else other tumor-inhibiting agents and/or classical antiinflammatory or antirheumatic agents. Furthermore, by reason of their immunomodulating properties, they are outstandingly suitable for use as adjuvants in vaccines.

EXAMPLES

The examples which follow explain the invention but without limiting its scope. The structures of the compounds described hereinafter were verified by elemental analyses, IR and $^1$H NMR spectra and, in a few cases, also by $^{13}$C and $^{31}$P NMR spectra.

EXAMPLE 1

Diethyl 3-phenyl-2-isoxazolin-5-ylphosphonate (by procedure (a))

(a) Benzhydroxamoyl chloride 58.7 g (0.44 mol) of N-chlorosuccinimide are suspended in 300 ml of dichloromethane with the addition of 2 ml of pyridine, and 48.5 g (0.4 mol) of benzaldoxime, dissolved in 150 ml of dichloromethane are added dropwise while stirring and while the exothermic reaction takes place. The reaction mixture is subsequently refluxed for 30 minutes, then cooled and employed directly for the cycloaddition.

(b) Cycloaddition with diethyl vinylphosphonate 72.2 g (0.44 mol) of diethyl vinylphosphonate, dissolved in 100 ml of dichloromethane, are added to the solution prepared as in (a), and then, while stirring at room temperature, 61.2 ml (0.44 mol) of triethylamine dissolved in 200 ml of dichloromethane are added dropwise within 6 hours. The mixture is left to stand at room temperature overnight, filtered and extracted by shaking successively with aqueous sodium bicarbonate solution, 1 N citric acid solution and several times with water. After drying and concentration, 122 g of a yellow oil remain and can be obtained analytically pure by column chromatography on silica gel (eluent: ethyl acetate/petroleum ether 1:1; vol.) or by distillation under reduced pressure.

$^1$H-NMR (CDCl$_3$): δ=1.2-1.6 (2t, J=7 Hz, 6H, P(OEt)$_2$), 3.4-4.6 (m, 6H, 4-H and P(OEt)$_2$), 4.75-5.25 (mc, 1H, 5-H), 7.45-8.1 ppm (m, 5H, Phenyl-H).

C$_{13}$H$_{18}$NO$_4$P (283.3)

Analysis: Calc.: C 55.12, H 6.41, N 4.95. Found: C 55.50, H 6.70, N 5.25.

EXAMPLE 2

Diethyl 3-phenyl-2-isoxazolin-5-ylmethylphosphonate

In analogy to Example 1, 76.7 g of an oily crude product are obtained starting from 30.3 g (0.25 mol) of benzaldoxime, 36.7 g (0.275 mol) of N-chlorosuccinimide, 49 g (0.275 mol) of diethyl allylphosphonate and 38.2 ml (0.275 mol) of triethylamine and can be purified as described in Example 1.

$^1$H-NMR (CDCl$_3$): δ=1.1-1.45 (2t, J=7 Hz, 6H, P(OEt)$_2$), 1.8-2.8 (m, 2H, CH$_2$-P), 3.15-3.49 (m, 2H, 4-H), 3.75-4.3 (m, 4H, P(OEt)$_2$), 4.65-5.1 (mc, 1H, 5-H), 7.05-7.6 ppm (m, 5H, Phenyl-H).

EXAMPLE 3

Diethyl 3-(4-chlorophenyl)-2-isoxazolin-5-ylphosphonate

The compound is prepared in analogy to Example 1 from 23.34 g (0.15 mol) of 4-chlorobenzaldoxime, 22 g of N-chlorosuccinimide, 27.1 g of diethyl vinylphosphonate and 22.9 ml of triethylamine, resulting in 49 g of oily product.

$^1$H-NMR (CDCl$_3$): δ=1.19-1.5 (2t, J=7 Hz, 6H, P(OEt)$_2$), 3.2-4.45 (m, 6H, 4-H and P(OEt)$_2$), 4.55-5.0 (mc, 1H, 5-H), 7.2 and 7.45 ppm (AA'BB', 4H, Aryl-H).

EXAMPLE 4

Diethyl 3-(4-chlorophenyl)-2-isoxazolin-5-ylmethylphosphonate

Preparation is carried out as in Example 1 from 23.34 g of 4-chlorobenzaldoxime, 22 g of N-chlorosuccinimide, 29.5 g of diethyl allylphosphonate and 22.9 ml of triethylamine in dichloromethane and provides 52 g of oily product.

$^1$H-NMR (CDCl$_3$): δ=1.15-1.5 (2t, J=7 Hz, 6H, P(OEt)$_2$), 1.8-2.8 (m, 2H, CH$_2$-P), 3.15-3.45 (m, 2H, 4-H), 3.7-4.35 (m, 4H, P(OEt)$_2$), 4.7-5.1 (mc, 1H, 5-H), 7.22 and 7.5 ppm (AA'BB', 4H, Aryl-H).

EXAMPLE 5

Dimethyl 3-phenyl-2-isoxazolin-5-ylphosphonate

As in Example 1, 58.2 g (0.374 mol) of benzhydroxamoyl chloride (prepared as in Example 1a) from benzaldoxime and N-chlorosuccinimide in dimethylformamide, then, after addition of ice-water, extracted with diethyl ether and isolated as oil), 50.9 g (0.374 mol) of dimethyl vinylphosphonate and 52 ml (0.374 mol) of triethylamine in 1.1 l of diethyl ether are reacted. The oil obtained after the usual working up in a crude yield of 68.5 g can be purified by crystallization from methanol/diethyl ether or dichloromethane/diethyl ether, resulting in 60.6 g of pure product with a melting point of 75° to 77° C.

$^1$H-NMR (CDCl$_3$): δ=3.25–3.9 (m, 8H, 4-H and P(OMe)$_2$ as d, J=10 Hz at 3.77), 4.55–5.05 (mc, 1, 5-H), 7.1–7.65 ppm (m, 5H, Phenyl-H).

C$_{11}$H$_{14}$NO$_4$P (255.3)

Analysis: Calc.: C 51.77, H 5.53, N 5.49. Found: C 51.79, H 5.62, N 5.45.

EXAMPLE 6

Diethyl 3-(2-pyridyl)-2-isoxazolin-5-ylphosphonate (a) 2-Pyridylhydroxamoyl chloride hydrochloride Preparation is carried out by chlorination of pyridine-2-carbaldoxime in dichloromethane based on a literature procedure (Bull. Soc. Chim. France 1962, 2215). The product is crystallized directly from the reaction solution by addition of diethyl ether after removal of the excess chlorine by brief evacuation. The yield is 95.5%. The melting point is 173° to 178° C. (decomposition).

(b) Cycloaddition with diethyl vinylphosphonate (by procedure (a))

77.8 g (0.4 mol) of the hydroxamoyl chloride prepared in (a) are suspended in 1 of tetrahydrofuran, 72.2 g (0.44 mol) of diethyl vinylphosphonate are added, and one half of a solution of 111.2 ml (0.8 mol) of triethylamine in 200 ml of tetrahydrofuran is added dropwise with vigorous stirring in one hour, followed by the remainder in a further 5 hours. The mixture is stirred overnight and filtered, the filtrate is concentrated and water is added, and the product is extracted with ethyl acetate. 111 g of oily isoxazoline are obtained.

$^1$H-NMR (CDCl$_3$): δ=1.3 (tb, J=7 Hz, 6H, P(OEt)$_2$), 3.4–4.45 (m, 6H, 4-H and P(OEt)$_2$), 4.6–5.05 (mc, 1H, 5-H), 7.0–8.0 (m, 3H, Pyridyl-H), 8.35–8.55 ppm (m, 1H, Pyridyl-6-H).

EXAMPLE 7

Diethyl 3-(4-pyridyl)-2-isoxazolin-5-ylphosphonate

Preparation is carried out in analogy to Example 6 from 17 g (0.088 mol) of 4-pyridylhydroxamoyl chloride hydrochloride, 15.8 g (0.096 mol) of diethyl vinylphosphonate and 26.6 ml (0.192 mol) of triethylamine. 17.8 g of oily product are obtained.

$^1$H-NMR (DMSO-d$_6$): δ=1.23 (tb, J=7 Hz, 6H, P(OEt)$_2$), 3.2–4.3 (m, 6H, 4-H and P(OEt)$_2$), 4.75–5.24 (mc, 1H, 5-H), 7.5 and 8.55 ppm AA'BB', 4H, Pyridyl-H).

EXAMPLE 8

3-(4-Methoxyphenyl)-2-isoxazolin-5-ylphosphonate

Reaction of 45.35 g (0.3 mol) of 4-methoxybenzaldoxime, 40 g (0.3 mol) of N-chlorosuccinimide, 54.1 g (0.33 mol) of diethyl vinylphosphonate and 46 ml (0.33 mol) of triethylamine in analogy to Example 1 yields 90.5 g of oily product.

$^1$H-NMR (CDCl$_3$): δ=1.3 (tb, J=7 Hz, 6H, P(OEt)$_2$), 3.15–4.4 (m, 9H, 4-H, OMe and P(OEt)$_2$), 4.5–4.95 (mc, 1H, 5-H), 6.75 and 7.43 ppm (AA'BB', 4H, Aryl-H).

EXAMPLE 9

Dimethyl 3-(3-phenoxyphenyl)-2-isoxazolin-5-ylphosphonate

In analogy to Example 1, 42.65 g (0.2 mol) of 3-phenoxybenzaldoxime, 29.4 g (0.22 mol) of N-chlorosuccinimide, 29.2 ml (0.22 mol) of dimethyl vinylphosphonate and 30.6 ml (0.22 mol) of triethylamine are reacted, and 66.4 g of oily product are obtained.

$^1$H-NMR (CDCl$_3$): δ=3.15–3.95 (m, 8H, 4-H and P(OMe)$_2$), 4.5–5.0 (mc, 1H, 5-H), 6.7–7.4 ppm (m, 9H, aromatic -H).

EXAMPLE 10

Dimethyl 3-(1-naphthyl)-2-isoxazolin-5-ylphosphonate

Preparation is carried out in analogy to Example 1 from 31.2 g (0.2 mol) of 1-naphthaldoxime, 29.4 g (0.22 mol) of N-chlorosuccinimide, 29.2 ml (0.22 mol) of dimethyl vinylphosphonate and 30.6 ml (0.22 mol) of triethylamine, with 56 g of oily compound being obtained.

$^1$H-NMR (CDCl$_3$): δ=3.4–4.1 (m, 8H, 4-H and P(OMe)$_2$), 4.6–5.1 (mc, 1H, 5-H), 7.1–7.9 (m, 6H, aromatic-H) 8.6–8.9 ppm (m, 1H, aromatic-H).

EXAMPLE 11

Diethyl 3-styryl-2-isoxazolin-5-ylphosphonate

The compound is prepared in analogy to Example 1 from 73.6 g (0.5 mol) of styrylaldoxime, 73.4 g (0.55 mol) of N-chlorosuccinimide, 90.2 g (0.55 mol) of diethyl vinylphosphonate and 76.4 ml (0.55 mol) of triethylamine. 153 g of oily product are obtained.

$^1$H-NMR (Methanol-d$_4$): δ=1.3 (tb, J=7 Hz, 6H, P(OEt)$_2$), 3.2–4.35 (m, 6H, 4-H and P(OEt)$_2$), 4.5–5.0 (mc, 1H, 5-H), 6.8 (sb, 2H, Ph—C$\underline{H}$=C$\underline{H}$—), 6.95–7.6 ppm (m, 5H, Aryl-H).

EXAMPLE 12

Diethyl 3-benzoyl-2-isoxazolin-5-ylphosphonate

The synthesis of benzoylhydroxamoyl chloride is known from the literature (for example: J. Heterocyclic Chem. 21 (1984), 1029). 45 g (0.245 mol) of this hydroxamoyl chloride are reacted as in Example 1 or 6 with 44.3 g (0.270 mol) of diethyl vinylphosphonate and 37.5 ml (0.270 mol) of triethylamine in a total of 600 ml of tert.butyl methyl ether. The usual working up provides 73.9 g of red-brown oil.

$^1$H-NMR (CDCl$_3$): δ=1.3 (tb, J=7 Hz, 6H, P(OEt)$_2$), 3.1–4.4 (m, 6H, 4-H and P(OEt)$_2$), 4.55–5.0 (mc, 1H, 5-H), 7.1–7.55 and 7.85–9.2 ppm (m, 5H, Aryl-H).

EXAMPLE 13

Methyl 3-phenyl-2-isoxazolin-5-yl(P-methyl)phosphinate (by procedure (a))

Preparation is carried out in analogy to Example 5 in diethyl ether using 11 g (0.07 mol) of benzhydroxamoyl chloride, 9.2 g (0.077 mol) of methyl vinyl(P-methyl)-phosphinate and 10.7 ml (0.077 mol) of triethylamine. After the usual working up, the aqueous wash phases are combined and extracted at pH 2 with dichloromethane, and this extract is dried and concentrated together with the ethereal phase. Crystallization of the residue from diethyl ether provides 12.2 g of product of melting point 72° to 74° C.

¹H-NMR (CDCl₃): δ=1.6 (d, J=15 Hz, 3H, P-Me), 3.45-4.15 (m, 5H, 4-H and P-OMe), 4.75-5.25 (mc, 1H, 5-H), 7.45-8.05 ppm (m, 5H, Aryl-H).

C₁₁H₁₄NO₃P (239.2)

Analysis: Calc.: C 55.23, H. 5.90, N 5.86. Found: C 55.25, H 6.00, N 5.91.

EXAMPLE 14

Methyl 3-(4-methoxyphenyl)-2-isoxazolin-5-yl(P-methyl)phosphinate 72.3 g of oily product are obtained in analogy to Example 1 from 45.35 g (0.3 mol) of 4-methoxybenzaldoxime, 40 g (0.3 mol) of N-chlorosuccinimide, 39.6 g (0.33 mol) of methyl vinyl(P-methyl)phosphinate and 46 ml (0.33 mol) of triethylamine.

¹H-NMR (CDCl₃): δ=1.5 (d, J=15 Hz, 3H, P-Me), 3.2-3.9 (m, 8H, 4-H, C-OMe and P-OMe), 4.5-4.95 (mc, 1H, 5-H), 6.75 and 7.43 ppm (AA'BB', 4H, Aryl-H).

EXAMPLE 15

Methyl 3-(4-methylphenyl)-2-isoxazolin-5-yl(P-methyl)phosphinate

In analogy to Example 1, 36.5 g of analytically pure product of melting point 96°-100° C. are obtained from 33.8 g (0.25 mol) of 4-tolualdoxime, 36.7 g (0.275 mol) of N-chlorosuccinimide, 33 g (0.275 mol) of methyl vinyl(P-methyl)phosphinate and 38.2 ml (0.275 mol) of triethylamine and after recrystallization from tert.butyl methyl ether.

¹H-NMR (CDCl₃): δ=1.5 (d, J=14 Hz, 3H, P-Me), 2.33 (s, 3H, Aryl-CH₃), 3.25-3.9 (m, 5H, 4-H and P-OMe), 4.5-4.95 (mc, 1H, 5-H), 7.05 and 7.4 ppm (AA'BB', 4H, Aryl-H).

C₁₂H₁₆NO₃P (253.2)

Analysis Calc.: C 56.92, H 6.37, N 5.53. Found: C 57.21, H 6.44, N 5.67.

EXAMPLE 16

Methyl 3-(1-naphthyl)-2-isoxazolin-5-yl(P-methyl)phosphinate 39.1 g (0.25 mol) of naphthaldoxime, 36.7 g (0.275 mol) of N-chlorosuccinimide, 33 g (0.275 mol) of methyl vinyl(P-methyl)phosphinate and 38.2 ml (0.275 mol) of triethylamine are reacted as in Example 1 to give 70 g of oily product.

¹H-NMR (CDCl₃): δ=1.55 (d, J=14 Hz, 3H, P-Me), 3.4-4.1 (m, 5H, 4-H and P-OMe), 4.5-4.95 (mc 1H, 5-H) 7.05-8.0 (m, 6H, Aryl-H) and 8.75 ppm (mc, 1H, Aryl-4-H).

EXAMPLE 17

3-Phenyl-2-isoxazolin-5-yldimethylphosphine oxide (by procedure (a))

Preparation is carried out in analogy to Example 1 by starting from 60.6 g (0.5 mol) of benzaldoxime, 73.45 g (0.55 mol) of N-chlorosuccinimide, 57.3 g (0.55 mol) of vinyldimethylphosphine oxide and 76.5 ml (0.55 mol) of triethylamine. After the usual working up, the product is recrystallized from. tert.butyl methyl ether. 64.4 g of pure product of melting point 153° C. are obtained.

¹H-NMR (CDCl₃): δ=1.4 and 1.6 (2d, J=12 Hz, 6H, PMe₂), 3.25-3.85 (AB of ABX, 2H, 4-H), 4.4-4.95 (mc, 1H, 5-H), 6.95-7.55 ppm (m, 5H, Aryl-H).

C₁₁H₁₄NO₂P (223.2)

Analysis: Calc.: C 59.19, H 6.32, N 6.28. Found: C 59.20, H 6.43, N 6.30.

EXAMPLE 18

Diethyl 3-phenyl-5-isoxazolylphosphonate (by procedure (b))

66.8 g (0.275 mol) of diethyl α-bromovinylphosphonate, dissolved in dichloromethane, and subsequently, within 5.5 hours, a solution of 76.4 ml (0.55 mol) of triethylamine in 250 ml of dichloromethane, are added dropwise to a solution of 0.25 mol of benzhydroxamoyl chloride in dichloromethane—prepared as described in Example 1a). The mixture is stirred overnight and worked up as in Example 1b), resulting in 76 g of oily product.

¹H-NMR (CDCl₃): δ=1.38 (tb, 6H, P(OEt)₂), 4.2 (dq, 4H, P(OEt)₂), 7.2 (d, J=1.5 Hz, 1H, 4-H), 7.3-7.9 ppm (m, 5H, Aryl-H).

EXAMPLE 19

Diethyl 3-(4-methoxyphenyl)-5-isoxazolylphosphonate

Preparation is carried out as in Example 18 from 30.2 g (0.2 mol) of 4-methoxybenzaldoxime, 26.7 g (0.2 mol) of N-chlorosuccinimide, 1 ml of pyridine, 48.6 g (0.2 mol) of diethyl α-bromovinylphosphonate and 61.2 ml (0.44 mol) of triethylamine in dichloromethane. After the usual working up, 65 g of a brown oil are obtained.

¹H-NMR (CDCl₃): δ=1.4 (tb, 6H, P(OEt)₂), 3.95 (s, 3H, OMe), 3.95-4.6 (m, 4H, P(OEt)₂), 7.0-7.4 (m, 3H, 4-H and Ar-H), 7.85-8.1 ppm (m, 2H, Ar-H).

EXAMPLE 20

Diethyl 3-(2-pyridyl)-5-isoxazolylphosphonate

In accordance with Examples 6 and 18, reaction of 38.6 g (0.2 mol) of 2-pyridylhydroxamoyl chloride hydrochloride (cf. Example 6a)) with 48.6 g (0.2 mol) of diethyl α-bromovinylphosphonate with dropwise addition of 83.4 ml (0.6 mol) of triethylamine in 1 l of tetrahydrofuran provides 50.9 g of oily product.

¹H-NMR (CDCl₃): δ=1.35 (tb, 6H, P(OEt)₂), 4.1 (dq, 4H, p(OEt)₂), 7.05-8.0 (m, 4H, pyridyl-Hand Isoxazole-4-H at 7.35 ppm), 8.35-8.6 ppm (m, 1H, Pyridyl-6-H).

EXAMPLE 21

Diethyl 3-(4-pyridyl)-5-isoxazolylphosphonate

4-Pyridylhydroxamoyl chloride hydrochloride is prepared in analogy to Example 6 or 7. Cyclization with diethyl α-bromovinylphosphonate and triethylamine is carried out as in Example 20 and provides the desired isoxazole as an oily product.

¹H-NMR (CDCl₃): δ=1.35 (tb, 6H, P(OEt)₂), 4.1 (dq, 4H, P(OEt)₂), 7.1 (d, J=1.8 Hz, 1H, 4-H), 7.55 and 8.55 ppm (AA'BB', 4H, Pyridyl-H).

EXAMPLE 22

Diethyl 3-propyl-2-isoxazolin-5-ylphosphonate (by procedure (a)) 42.7 g (0.26 mol) of diethyl vinylphosphonate and 1.1 ml of triethylamine are dissolved in 180 ml of tert.butyl methyl ether, 56.4 g (0.473 mol) of phenyl isocyanate are added, and a solution of 24.4 g (0.237 mol) of nitrobutane in 120 ml of tert.butyl methyl ether is added dropwise within 7 hours. The mixture is stirred for 3 days and, after addition of 30 ml of 2 N ethanolic ammonia solution, is stirred for a further 30 minutes and filtered, and the filtrate is diluted with ethyl acetate and washed successively with aqueous ammonia solution, water, 2 N HCl and again with water. After drying and concentration, 27.3 g of oily final product remain.

$^1$H-NMR (CDCl$_3$): δ=0.8–1.8 (m, 11H, p(OEt)$_2$ and CH$_3$—CH$_2$—), 2.15–2.5 (mc, 2H, —CH$_2$—), 2.8–3.5 (m, 2H, 4-H), 3.8–4.8 ppm (m, 5H, P(OEt)$_2$ and 5-H).

EXAMPLE 23

Dimethyl 3-benzyl-2-isoxazolin-5-ylphosphonate (by procedure (a))

13.5 ml (0.124 mol) of phenyl isocyanate, 9.5 g (0.07 mol) of dimethyl vinylphosphonate and 1 ml of triethylamine are introduced into 120 ml of toluene. A solution of 9.3 g (0.062 mol) of 2-phenylnitroethane and 1 ml of triethylamine dissolved in 150 ml of toluene is added dropwise in 5 hours, the mixture is stirred overnight and then for 30 minutes after addition of 30 ml of concentrated aqueous ammonia, precipitated diphenylurea is removed by filtration and washed with ethyl acetate, and the combined organic phases are extracted by shaking successively with water, 2 N hydrochloric acid and water, and are dried and concentrated. 13.9 g of reddish brown oil remain.

$^1$H-NMR (CDCl$_3$): δ=2.7–3.85 (m, 10H, 4-H, Benzyl-H and P(OMe)$_2$), 4.3–4.8 (mc, 1H, 5-H), 6.8–7.25 ppm (m, 5H, Aryl-H).

EXAMPLE 24

Methyl 3-benzyl-2-isoxazolin-5-yl(P-methyl)phosphinate

Preparation is carried out in analogy to Example 23 from 37.1 ml (0.34 mol) of phenyl isocyanate, 22.5 g (0.187 mol) of methyl vinyl(P-methyl)phosphinate, 4 ml of triethylamine and 25.7 g (0.17 mol) of 2-phenylnitroethane in toluene, resulting in 34 g of brown oil.

$^1$H-NMR (CDCl$_3$): δ=1.35 (d, J=14 Hz, 3H, P-Me), 2.7–3.75 (m, 7H, 4-H, Benzyl-H and P-OMe), 4.4–4.95 (mc, 1H, 5-H), 6.8–7.5 ppm (m, 5H, Aryl-H).

EXAMPLE 25

Methyl 3-tert.butyl-2-isoxazolin-5-yl(P-methyl)phosphinate 40.4 g (0.4 mol) of pivalaldoxime are converted in analogy to Example 1(a) with 58.7 g (0.44 mol) of N-chlorosuccinimide and 2 ml of pyridine in dichloromethane into the hydroxamoyl chloride which is subsequently reacted with 52.8 g (0.44 mol) of methyl vinyl(P-methyl)phosphinate and 61.2 ml (0.44 mol) of triethylamine, and worked up, as described in Example 1(b), the oily product being obtained with a yield of about 50%.

$^1$H-NMR (CDCl$_3$): δ=1.0–1.65 (m, 12H, tBu and P-Me), 2.8–3.75 (m, 5H, 4-H and P-OMe as d at 3.6 ppm) 4.25–4.7 ppm (mc, 1H, 5-H).

EXAMPLE 26

Diethyl 3-tert.butyl-2-isoxazolin-5-ylphosphonate

The procedure is analogous to that of Example 25 using 15.2 g (0.15 mol) of pivalaldoxime, 22.0 g (0.165 mol) of N-chlorosuccinimide, 0.5 ml of pyridine, 27.1 g (0.165 mol) of diethyl vinylphosphonate and 22.9 ml (0.165 mol) of triethylamine in dichloromethane. The product is obtained as an oil after the usual working up.

$^1$H-NMR (CDCl$_3$): δ=1.1–1.5 (15H, tbu at 1.2 ppm and P(OEt)$_2$), 2.95–3.5 (m, 2H, 4-H), 3.85–4.8 ppm (m, 5H, 5-H and P(OEt)$_2$).

EXAMPLE 27

Monoethyl 3-phenyl-2-isoxazolin-5-ylphosphonate (by procedure (c))

10 g (35.3 mmol) of the diethyl ester prepared as in Example 1 are dissolved in 140 ml of ethanol and, after addition of 140 ml of 1 N sodium hydroxide solution, stirred at room temperature for 30 hours. The ethanol is removed under reduced pressure, the aqueous phase is extracted with ether and then acidified with hydrochloric acid to pH 1 and extracted several times with dichloromethane. After washing with half-concentrated NaCl solution and concentration there remains a viscous oil which can be crystallized from diethyl ether. 7.2 g of pure product of melting point 84° to 91° C. are obtained.

$^1$H-NMR (CDCl$_3$): δ=1.35 (t, J=7 Hz, 3 H, P-OEt), 3.35–4.6 (m, 4H, 4-H and P-OEt), 4.7–5.2 (mc, 1H, 5-H), 7.4–8.1 (m, 5H, Phenyl-H), 12.1 ppm (sb, 1H, P-OH).

C$_{11}$H$_{14}$NO$_4$P (255.2)

Analysis: Calc.: C 51.77, H 5.53 , N 5.49. Found: C 51.97, H 5.54, N 5.26.

EXAMPLE 28

Monoethyl ammonium 3-(4-methoxyphenyl)-2-isoxazolin-5-ylphosphonate

The diethyl phosphonate of Example 8 is hydrolyzed as in Example 27 with 1.1 equivalents of sodium hydroxide solution, and the monoester which is formed is isolated in the acid form as an oily product (yield: 70%) and—as described in detail in Example 35—converted into the crystalline ammonium salt with a melting range of 141° to 154° C. (yield: 53%).

$^1$H-NMR (D$_2$O): δ=1.25 (tb, J=7 Hz, 3H, P-OEt), 3.1–4.25 (m, 7H, 4-H, P-OEt and OMe at 3.72 ppm), 4.4–4.9 (m, ca. 5H, 5-H and NH$_4^+$), 6.75 and 7.4 ppm (AA'BB', 4H, Aryl-H).

C$_{12}$H$_{19}$N$_2$O$_5$P (302.3)

Analysis: Calc.: C 47.68, H 6.34, N 9.27. Found C 47.67, H 6.14, N 8.60.

The isoxazolinephosphinic acids of the general formula

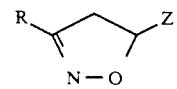

which are compiled as Examples 29 to 32 in Table 1 on page 37 were likewise obtained by procedure (c) from the corresponding methyl esters of Examples 14, 15, 24 and 16, respectively, in analogy to Example 27 by hydrolysis with excess sodium hydroxide solution and were purified by crystallization as free acids or conversion into the crystalline ammonium salts (in ethanol with ethanolic ammonia solution). Furthermore, the phosphinic acid of Example 31 was also obtained by ester cleavage with hydrogen bromide (HBr) in glacial acetic acid in analogy to Example 34.

EXAMPLE 33

3-tert.butyl-2-isoxazolin-5-ylphosphonic acid (by procedure (c))

39.6 g (0.15 mol) of the compound from Example 26 are dissolved in a mixture of 100 ml of 33% strength HBr/glacial acetic acid solution and 50 ml of glacial acetic acid.

The reaction mixture is left to stand at room temperature for 3 days and then concentrated, methanol is distilled over several times, and the remaining residue is extracted by stirring with tert.butyl methyl ether, resulting in 20.8 g of analytically pure product of melting point 195° to 197° C.

$^1$H-NMR (DMSO-d$_6$) δ=1.1 (s, 9H, tBu), 2.7–3.4 (m, 2H, 4-H), 4.1–4.6 (mc, 1H, 5-H), 10.5 ppm (sb, 2H, P-OH).

C$_7$H$_{14}$NO$_4$P (207.2)

Analysis: Calc.: C 40.59, H 6.81, N 6.76. Found: C 40.28, H 6.95, N 6.83.

EXAMPLE 34

3-Phenyl-2-isoxazolin-5-ylphosphonic acid (by procedure (c))

122 g of the crude diethyl ester prepared as in Example 1 are dissolved in 400 ml of a 2 N solution of HBr in glacial acetic acid, the solution is left at room temperature for 2 days and then heated at 40° C. for 2 hours, the solvent is removed under reduced pressure and methanol is distilled over several times. Recrystallization of the residue from dichloromethane provides 60 g of the analytically pure phosphonic acid of melting point 183° to 184° C.

$^1$H-NMR (DMSO-d$_6$): δ=3.1–3.9 (m, 2H, 4-H), 4.4–4.95 (mc, 1H, 5-H), 7.2–7.8 (m, 5H, Phenyl-H), 10.6 ppm (sb, 2H, P-OH). C$_9$H$_{10}$NO$_4$P (227.2)

Analysis: Calc.: C 47.59, H 4.44, N 6.17. Found: C 47.66, H 4.44, N 6.09.

Examples 35 to 38 relate to various salts of 3-phenyl-2-isoxazolin-5-ylphosphonic acid from Example 34.

EXAMPLE 35

Diammonium salt of Example 34

10 g of the phosphonic acid from Example 34 are dissolved in 150 ml of methanol, the solution is made alkaline with alcoholic ammonia solution, the salt which forms is precipitated as crystals by cooling and, if necessary, seeding, and precipitation is completed by addition of tert.butyl methyl ether. 10 g of diammonium salt with a melting point of 197° to 202° C. are obtained.

C$_9$H$_{16}$N$_3$O$_4$P (261.2)

Analysis: Calc.: C 41.38, H 6.17, N 16.09. Found: C 41.70, H 6.16, N 15.65.

The salt can also be prepared easily from the crude acid of Example 34. For this purpose, the hydrolyzate obtained from 0.15 mol of diethyl ester of Example 1 is dissolved in water, extracted twice with a solution of 80 ml of Amberlite ®LA-2 (OH form) in 240 ml of ethyl acetate, the organic phase is washed with water, and the acid is reextracted as diammonium salt by shaking three times with 100 ml of half-concentrated aqueous ammonia solution each time. The aqueous phase is washed several times with ethyl acetate and concentrated, and the pure salt is obtained in crystalline form by extracting by stirring in acetone or ethanol. If desired, the free phosphonic acid can be recovered, after suspending the salt in methanol, by addition of excess Amberlyst ®15 in the H$^+$ form and concentration of the alcoholic solution.

TABLE 1

| Example | R | Z | Melting point (°) | $^1$H NMR (DMSO-d$_6$), δ(ppm)* | Analysis |
|---------|---|---|-------------------|----------------------------------|----------|
| 29 | 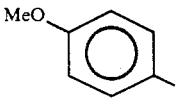 | 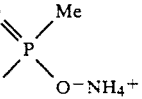 | 143–147 | (in Methanol-d$_4$)<br>1.25 (d, J=14 Hz, 3H, P—Me)<br>3.1–3.9 (m, 5H, 4-H and OMe and 3.7)<br>4.2–5.1 (m, ~5H, 5-H and NH$_4$⊕)<br>6.75 and 7.45 (AA', BB', 4H, Aryl-H) | C$_{11}$H$_{17}$N$_2$O$_4$P (272.2)<br>Calc.: C 48.53 H 6.30 N 10.29<br>Found: C 48.31 H 5.88 N 9.80 |
| 30 | 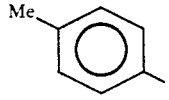 | 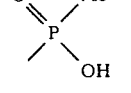 | 172–176 | 1.35 (d, J=14 Hz, 3H, P—Me)<br>2.8 (s, 3H, Aryl-CH$_3$)<br>3.2–3.85 (m, 2H, 4-H)<br>4.35–4.9 (mc, 1H, 5-H),<br>7.1 and 7.45 (AA', BB', 4H, Aryl-H),<br>9.4 (sb, 1H, P—OH) | C$_{11}$H$_{14}$NO$_3$P (239.2)<br>Calc.: C 55.23 H 5.90 N 5.86<br>Found: C 55.16 H 5.57 N 5.89 |
| 31 | Ph—CH$_2$— | 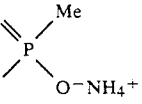 | 139 | in D$_2$O:<br>1.15 (d, J=13 Hz, 3H, P—Me),<br>2.7–3.35 (m, 2H, 4-H),<br>3.6 (sb, 2H, Benzyl),<br>4.1–4.8 (mc, ~5H, 5-H and NH$_4$$^+$),<br>7.0–7.4 (m, 5H, Aryl-H). | C$_{11}$H$_{17}$N$_2$O$_3$P (256.2)<br>Calc.: C 51.56 H 6.69 N 10.93<br>Found: C 51.55 H 6.81 N 10.89 |
| 32 | 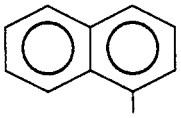 | 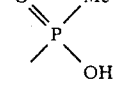 | 139–140 | 1.45 (d, J=14 Hz, 3H, P—Me)<br>3.4–4.15 (m, 2H, 4-H)<br>4.5–5.05 (mc, 1H, 5-H)<br>7.3–8.15 (m, 6H, Aryl-H)<br>8.4–9.0 (m, 2H, Aryl-4-H and P—OH) | C$_{14}$H$_{14}$NO$_3$P (275.25)<br>Calc.: C 61.09 H 5.13 N 5.09<br>Found: C 60.61 H 5.04 N 5.06 |

The ammonium salts are generally readily crystallizable but, on exposure to heat, tend to eliminate ammonia to a noticeable extent. Hence use of elevated temperatures should be avoided when drying them, especially under reduced pressure.

EXAMPLE 36

Disodium salt of Example 34

4.54 g (20 mmol) of the phosphonic acid of Example 34 are dissolved in 40 ml of methanol, and 1.6 g (40 mmol) of sodium hydroxide in about 40 ml of methanol are added, resulting in the formation of a gel-like precipitate. The mixture is boiled briefly and left to stand at room temperature for 3 days, and the product is filtered off with suction and dried. 3.85 g of the disodium salt are obtained with a melting point >300° C. Further product can be isolated from the mother liquor.

$C_9H_8NNa_2O_4P$ (271.1)

Analysis: Calc.: C 39.87, H 2.97, N 5.17, Na 16.96. Found: C 39.77, H 2.89, N 5.12, Na 17.20.

EXAMPLE 37

Monopotassium salt of Example 34

4.54 g (20 mmol) of 3-phenyl-2-isoxazolin-5-ylphosphonic acid are dissolved in 120 ml of methanol, and 2.76 g (20 mmol) of potassium carbonate are added. After brief boiling, the solution is cooled, saturated with $CO_2$ by introducing dry ice, and left in a refrigerator overnight, and the precipitate which has formed is filtered off with suction and dried. 4.2 g of monopotassium salt of melting point >300° C. are obtained.

$C_9H_9KNO_4P$ (265.3)

Analysis: Calc.: C 40.75, H 3.42, N 5.28, K 14.74. Found: C 40.51, H 3.30, N 5.48, K 15.20.

EXAMPLE 38

Dilysinium salt of Example 34

7.3 g (50 mmol) of L-lysine dissolved in 100 ml of methanol are added to a heated solution of 5.7 g (25 mmol) of the phosphonic acid from Example 34 in 150 ml of methanol. The mixture is boiled briefly and, after standing at room temperature for 2 hours, the precipitate is filtered off with suction, washed successively with methanol and tert.butyl methyl ether and dried, resulting in 11.1 g of salt of melting point 217° to 218° C.

$^1$H-NMR ($D_2O$): $\delta$=1.2-2.2 (m, 12H,Lysine-$CH_2$), 2.75-3.85 (m, 8H, 4-H,Lysine-CHN and —$CH_2$N), 4.3-4.95 (ca. 13H, 5-H and HDO), 7.3-7.85 ppm (m, 5H, Aryl-H).

$C_{21}H_{38}N_5O_8P$ (519.5)

Analysis: Calc.: C 48.55, H 7.37, N 13.48. Found: C 47.92, H 7.24, N 12.94.

The isoxazoline- and isoxazolephosphonic acids of the general formula

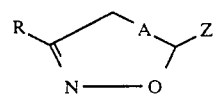

which are compiled as Examples 39 to 54 in Table 2 on pages 43 to 45 were likewise prepared by procedure (c) from the corresponding methyl or ethyl esters by reaction with HBr in glacial acetic acid as in Example 34 and were purified by chromatography, crystallization as acids or conversion into the diammonium salts in analogy to Example 35. The hydrobromide of Example 42 was recrystallized from methanol/tert.butyl methyl ether.

EXAMPLE 55

3-Phenyl-2-isoxazolin-5-yl(P-ethoxy)phosphonic acid pyrrolidide (by procedure (d))

8.5 g (0.03 mol) of the diethyl ester from Example 1 are dissolved in 150 ml of ethanol, 24.5 ml of pyrrolidine are added, and the mixture is refluxed for 10 hours. It is concentrated, and 8.5 g of the monoester monoamide are obtained in the form of an oil after purification by chromatography on silica gel (eluent: dichloromethane/methanol 5:1).

TABLE 2

| Example | R | Z | A | Melting point (°C.) | 1H NMR (DMSO d6), δ(ppm)* | Analysis |
|---|---|---|---|---|---|---|
| 39 | C6H5 | —CH2—P(OH)2 with C=O | CH2—CH | 209–218 | 1.7–2.35 (m, 2H, CH2—P), 3.0–3.5 (m, 2H, 4-H), 4.45–5.05 (mc, 1H, 5-H), 7.1–7.6 (m, 5H, Phenyl-H), 8.1 (sb, 2H, P(OH)2). | C10H12NO4P × 1/20 H2O (242.1) Calc.: C 49.63 H 5.04 N 5.79 Found: H2O 0.36 C 48.93 H 4.96 N 5.82 |
| 40 | 4-Cl-C6H4 | —P(OH)2 with C=O | CH2—CH | 207 | 3.0–3.9 (m, 2H, 4-H), 4.4–4.85 (mc, 1H, 5-H), 7.35 and 7.6 (AA' BB', 4H Aryl-H), 10.2 (sb, 2H, P(OH)2). | C9H9NO4Cl P (261.6) Calc.: C 41.32 H 3.47 N 5.36 Found: C 40.64 H 3.30 N 4.92 |
| 41 | 4-Cl-C6H4 | —CH2—P(OH)2 with C=O | CH2—CH | 203 | 1.75–2.3 (m, 2H, CH2—P), 2.9–3.6 (m, 2H, 4-H), 4.5–5.1 (mc, 1H, 5-H), 7.36 and 7.6 (AA' BB', 4H, Aryl-H), 9.4(sb, 2H, P(OH)2). | C10H11NO4Cl P (275.6) Calc.: C 43.58 H 4.02 N 5.08 Found: C 43.91 H 3.87 N 5.12 |
| 42 | 2-Pyridyl × HBr | —P(OH)2 with C=O | CH2—CH | 210–225 (Decomp.) | 3.15–3.95 (m, 2H, 4-H), 4.5–5.0 (mc, 1H, 5-H), 7.35–8.2 and 8.4–8.7 (m, 4H, Pyridyl-H), 10.8 (sb, 3H, P(OH)2 and NH) | C8H10N2O4Br P (309.6) Calc.: C 31.09 H 3.26 N 9.06 Found: C 30.75 H 3.16 N 9.01 |
| 43 | 2-Pyridyl | —P(ONH4)2 with C=O | CH2—CH | 192–194 | in D2O: 3.1–3.9 (m, 2H, 4-H), 4.5–5.1 (m, ~9H, 2 NH4+ u. 5-H) 7.47 and 8.45 (AA' BB', 4H, Pyridyl-H) | C8H15N4O4P (262.2) Calc.: C 36.65 H 5.77 N 21.37 Found: C 37.05 H 5.54 N 20.92 |
| 44 | 4-PhO-C6H4 | —P(OH)2 with C=O | CH2—CH | 186–193 | 3.0–3.85 (m, 2H, 4-H), 4.35–4.85 (mc, 1H, 5-H), 6.7–7.5 (m, 9H, Aryl-H), 8.8 (sb, 2H, P(OH)2). | C15H14NO5P (319.3) Calc.: C 56.43 H 4.42 N 4.39 Found: C 55.94 H 4.31 N 4.48 |
| 45 | 2-naphthyl | —P(OH)2 with C=O | CH2—CH | 170–209 (Zers.) | 3.3–4.1 (m, 2H, 4-H), 4.45–4.95 (mc, 1H, 5-H), 7.25–8.05 (m, 6H, aromatic H), 8.5–8.9 (m, 1H, aromatic H), 10.3 (sb, 2H, P(OH)2). | C13H12NO4P (277.2) Calc.: C 56.33 H 4.36 N 5.05 Found: C 55.55 H 4.35 N 5.64 |

TABLE 2-continued

| Example | R | Z | A | Melting point (°C.) | $^1$H NMR (DMSO d$_6$), δ(ppm)* | Analysis |
|---|---|---|---|---|---|---|
| 46 | C$_6$H$_5$ | O=P(OH)$_2$ | CH=C | 199-206 | 7.2-8.05 (m, 6H, Aryl-H and 4-H at d, J=1.8 Hz at 7.3), 9.8 (sb, 2H, P(OH)$_2$). | C$_9$H$_8$NO$_4$P (225.1) Calc.: C 48.01 H 3.58 N 6.22 Found: C 47.77 H 3.50 N 6.29 |
| 47 | CH$_3$—CH$_2$—CH$_2$ | O=P(ONH$_4$)$_2$ | CH$_2$—CH | 140-143 | in D$_2$O: 0.9 (t, J=6 Hz, CH$_3$), 1.2-1.8 (m, 2H, CH$_2$), 2.1-2.5 (m, 2H, CH$_2$), 2.75-3.4 (m 2H, 4-H), 4.0-4.5 (mc, 1H, 5-H), 4.7 (2 NH$_4^+$) | C$_6$H$_{18}$N$_3$O$_4$P (227.2) Calc.: C 31.72 H 7.98 N 18.49 Found: C 31.73 H 7.90 N 17.82 |
| 48 | MeO—C$_6$H$_4$— | O=P(OH)$_2$ | CH$_2$—CH | 204-206 | 3.0-3.85 (m, 5H, 4-H and OMe at 3.68), 4.25-4.75 (mc, 1H, 5-H), 6.77 and 7.4 (AA' BB', 4H, Aryl-H) 9.6 (sb, 2H, P(OH)$_2$). | C$_{10}$H$_{12}$NO$_5$P (257.2) Calc.: C 46.70 H 4.70 N 5.45 Found: C 46.28 H 4.49 N 5.44 |
| 49 | C$_6$H$_5$—CH$_2$— | O=P(OH)$_2$ | CH$_2$—CH | 155-159 | 2.35-3.35 (m, 2H, 4-H), 3.57 (sb, 2H, Benzyl-H), 4.1-4.6 (mc, 1H, 5-H), 6.9-7.35 (m, 5H, Aryl-H), 9.8 (sb, 2H, P(OH)$_2$). | C$_{10}$H$_{12}$NO$_4$P (241.2) Calc.: C 49.80 H 5.02 N 5.81 Found: C 49.81 H 4.88 N 5.80 |
| 50 | 2-pyridyl | O=P(OH)$_2$ | CH=C | 222-224 | in D$_2$O: 4.6 (sb, ~8H, 2 NH$_4^+$), 6.88 (d, J=1.5 Hz, 1H, 4-H) 7.1-7.85 (m, 3H, Pyridyl-H), 8.2-8.5 (mc, 1H, Pyridyl-6-H). | C$_8$H$_{13}$N$_4$O$_4$P (260.2) Calc.: C 36.92 H 5.04 N 21.52 Found: C 36.76 H 5.01 N 21.00 |
| 51 | 3-pyridyl | O=P(ONH$_4$)$_2$ | CH=C | 238-240 | in CF$_3$CO$_2$H: 7.65 (d, J=2 Hz, 1H, 4-H), 8.55 and 8.95 (AA' BB', 4H, Pyridyl-H). | C$_8$H$_{13}$N$_4$O$_4$P (260.2) Calc.: C 36.92 H 5.04 N 21.52 Found: C 36.47 H 5.19 N 20.80 |
| 52 | Ph—CH=CH— | O=P(OH)$_2$ | CH$_2$—CH | 191-193 | 2.95-3.7 (m, 2H, 4-H), 4.3-4.8 (mc, 1H, 5-H), 6.9 (sb, 2H, Ph—CH=CH), 7.0—7.6 (m, 5H, Aryl-H), 9.2 (sb, 2H, P(OH)$_2$). | C$_{11}$H$_{12}$NO$_4$P (253.2) Calc.: C 52.18 H 4.78 N 5.53 Found: C 51.96 H 4.62 N 5.54 |
| 53 | Ph—C(=O)— | O=P(ONH$_4$)$_2$ | CH$_2$—CH | 138-168 (Decomp.) | in D$_2$O: 3.1-3.95 (m, 2H, 4-H) 4.45-5.0 (m, ~9H,5-H and 2NH$_4^+$) 7.25-8.1 (m, 5H, Aryl-H). | C$_{10}$H$_{16}$N$_3$O$_5$P (289.2) Calc.: C 41.53 H 5.58 N 14.53 Found: C 41.05 H 5.37 N 13.63 |

TABLE 2-continued
| Example | R | Z | A | $^1$H NMR (DMSO $d_6$), δ(ppm)* | Melting point (°C.) | Analysis |
|---|---|---|---|---|---|---|
| 54 |  MeO— | —P(ONH$_4$)$_2$ ‖ O | CH=C | in D$_2$O: 3.7 (s, 3H, OMe) 6.6–6.95 (m, 3H, 4-H and 2 Ar—H) 7.55 (2H, Ar—H) | 187–190 | C$_{10}$H$_{16}$N$_3$O$_5$P (289.2) Calc.: C 41.53 H 5.58 N 14.53 Found: C 40.78 H 5.70 N 14.29 |

$^1$H-NMR (CDCl$_3$): δ=1.25 (tb, J=7 Hz, 3H, P-OEt), 1.7-2.2 (m, 4H, Pyrrolidine-CH$_2$), 3.05-4.35 (m, 8H, Pyrrolidine-N-CH$_2$, 4-H and P-OEt), 4.55-5.05 (mc, 1H, 5-H), 7.4-7.95 ppm (m, 5H, Aryl-H).

EXAMPLE 56

N-[3-Phenyl-2-isoxazolin-5-yl(P-ethoxy)phosphonoyl]glycine benzyl ester (by procedure (e))

14.6 g (0.057 mol) of the monoester from Example 27 are suspended in 150 ml of dry toluene, 11.7 g (0.057 mol) of phosphorus pentachloride are added, and the mixture is refluxed for 1 hour. After concentration under reduced pressure there remains a viscous oil to which, dissolved in 150 ml of tetrahydrofuran and cooled in ice, 23.5 ml (0.168 mol) of triethylamine and 18.9 g (0.056 mol) of glycine benzyl ester as toluenesulfonate are added, and the mixture is stirred at room temperature for 14 hours. It is diluted with ethyl acetate and washed successively with aqueous sodium bicarbonate and potassium bisulfate solutions and several times with water. The oil obtained after drying and concentration is crystallized from diethyl ether and provides 7.8 g of pure product of melting point 91° to 103° C.

$^1$H-NMR (CDCl$_3$): δ=1.05-1.5 (2t, 3H, P-OEt), 3.2-4.25 (m, 7H, P-OEt, 4-H, Gly-CH$_2$ and NH), 4.55-5.1 (m, 3H, 5-H and Benzyl-CH$_2$), 7.05-7.6 ppm (m, 10H, Aryl-H).

C$_{20}$H$_{23}$N$_2$O$_5$P (402.4)

Analysis: Calc.: C 59.70, H 5.76, N 6.96. Found: C 59.85, H 5.79, N 6.93.

EXAMPLE 57/58

N-[3-Phenyl-2-isoxazolin-5-yl(P-methyl)phosphinoyl]glycine benzyl ester (by procedure (e))

1.1 g (5 mmol) of 3-phenyl-2-isoxazolin-5-yl(P-methyl)phosphinic acid are dissolved in 20 ml of pyridine and, while cooling in ice, 1.5 g (7 mmol) of mesitylsulfonyl chloride and 0.5 g (7 mmol) of tetrazole are added, and the mixture is then stirred at room temperature for 30 minutes. 1.7 g (5 mmol) of glycine benzyl ester toluenesulfonate are added, and stirring at room temperature is continued with the course of the reaction being followed by thin-layer chromatography. After the reaction is complete, water and half-concentrated potassium bisulfate solution are added to pH 2, the mixture is extracted three times with dichloromethane, and the organic phase is washed with water, dried and concentrated. The pure product is obtained with a melting point of 132° to 135° C. by chromatography on silica gel with dichloromethane/methanol mixtures as mobile phases.

$^1$H-NMR (CDCl$_3$): δ=1.45-1.63 (each d, J=15 Hz, 3H, P-Me), 3.2-3.95 (m, 5H, 4-H, Gly-CH$_2$ and NH), 4.5-5.1 (m, 3H, 5-H at 4.8 ppm and Bzl-CH$_2$ at 5.0 ppm), 7.05-7.65 ppm (m, 10H, Aryl-H).

C$_{19}$H$_{21}$N$_2$O$_4$P (372.4)

Analysis: Calc.: C 61.29, H 5.69, N 7.52. Found: C 60.64, H 5.81, N 7.16.

The same compound was prepared in an alternative way, as Example 58, from 7.5 g (33 mmol) of 3-phenyl-2-isoxazolin-5-yl(P-methyl)phosphinic acid, 6.9 g (33 mmol) of phosphorus pentachloride, 11.1 g (33 mmol) of glycine benzyl ester toluenesulfonate and 13.9 ml (0.1 mol) of triethylamine in analogy to Example 56, and was purified by recrystallization from tert.butyl methyl ether. Its identity with the product described above was confirmed by analysis.

EXAMPLE 59

3-Phenyl-2-isoxazolin-5-ylphosphonic tetra methyldiamide (by procedure (a))

Preparation is carried out in analogy to Example 1 from 12.1 g (0.1 mol) of benzaldoxime, 14.7 g (0.11 mol) of N-chlorosuccinimide, 0.5 ml of pyridine, 17.8 g (0.11 mol) of vinylphosphonic tetramethyldiamide and 13.9 ml (0.1 mol) of triethylamine. 24.3 g of an oily crude product are obtained and purified by distillation under reduced pressure (boiling point: 145° to 150° C. at 0.133 mbar).

$^1$H-NMR (CDCl$_3$): δ=2.7 (2d, J=9 Hz, 12H, NMe$_2$), 3.2-3.85 (m, 2H, 4-H), 4.75-5.25 (mc, 1H, 5-H), 7.1-7.65 ppm (m, 5H, Aryl-H).

C$_{13}$H$_{20}$N$_3$O$_2$P (281.3)

Analysis: Calc.: C 55.51, H 7.17, N 14.94. Found: C 55.99, H 7.29, N 14.64.

EXAMPLE 60

Dimethyl (+)- and (−)-3-phenyl-2-isoxazolin-5-ylphosphonate (by procedure (g))

1.5 g of the racemic dimethyl ester from Example 5 are separated into the two enantiomers by chromatography on a triacetylcellulose column which is 95 cm long and has a diameter of 5 cm using ethanol/hexane mixtures as mobile phases, with mixed fractions which result being subjected to rechromatography.

(a) (+) isomer: Oil, [α]$_D^{20}$= +214.2° (c=2.0 in methanol), enantiomeric purity: >99% (from HPLC analysis)

(b) (−) isomer: Oil, [α]$_D^{20}$ = −198.5° (c=2.0 in methanol), enantiomeric purity: >95% (from HPLC analysis)

The corresponding enantiomerically pure phosphonic acids are obtained by ester cleavage of the two antipodes with acid in analogy to Example 34 and recrystallization from acetone, and all their properties coincide with the compounds described in Examples 61 and 62 which follow.

EXAMPLE 61

(+)-3-Phenyl-2-isoxazolin-5-ylphosphonic acid (by procedure (g))

22.7 g (0.1 mol) of the racemic phosphonic acid from Example 34 are dissolved in 150 ml of hot methanol and added to a solution of 59 g (0.2 mol) of (−)-cinchonidine in 500 ml of isopropanol and 50 ml of methanol at 50° C. On slow cooling to 0° C., 21 g of salt crystallize out. A further 3 g of the salt are obtained by addition of acetone to the mother liquor. The solid is recrystallized from methanol/acetone, and the phosphonic acid is liberated from the salt, which is obtained with an isomeric purity >98%, using an acidic ion exchanger, for example Amberlyst ®15, and, after further crystallization from acetone, has an enantiomeric purity of >99% according to HPLC analysis.

Melting point: 220° C. (decomposition)
[α]$_D^{20}$= +204.3° (c=2.0 in methanol)

EXAMPLE 62

(−)-3-Phenyl-2-isoxazolin-5-ylphosphonic acid (by procedure (g))

45.3 g (0.3 mol) of (−)-norephedrine are dissolved in 500 ml of hot methanol and, at 50° C., a solution of 34.1 g (0.15 mol) of racemic phosphonic acid from Example 34 in 100 ml of methanol are added. The mixture is allowed to crystallize while slowly cooling to 0° C. The 22 g of the norephedrinium salt obtained in this way are recrystallized from methanol. The phosphonic acid is liberated with an acidic ion exchanger and crystallized as described in Example 61. HPLC analysis shows the enantiomeric purity to be >99%.

Melting point: 218° C. (decomposition)
$[\alpha]_D^{20} = -204.7°$ (c=2.0 in methanol)

EXAMPLE 63

3-Phenyl-2-isoxazolin-5-yl(P-methyl)phosphinic acid (by procedure (c))

10.3 g of the phosphinic acid of melting point 162° to 167° C. are obtained in analogy to Example 27 from 12 g (0.05 mol) of the methyl ester described in Example 13.

$^1$H-NMR (DMSO-d$_6$): δ=1.45 (d, J=15 Hz, 3H, P-Me), 3.3–4.05 (m, 2H, (4-H), 4.6–5.15 (mc, 1H, 5-H), 7.5–8.1 (m, 5H, Aryl-H), 10.0 ppm (sb, 1H, P-OH).

$C_{10}H_{12}NO_3P$ (225.2)

Analysis: Calc.: C 53.34, H 5.37, N 6.22. Found: C 53.39, H 5.43, N 6.20.

EXAMPLE 64

3-tert.Butyl-2-isoxazolin-5-yl(P-methyl)phosphinic acid (by procedure (c))

10 g of the methyl ester from Example 25 provide, on reaction as in Example 34 and recrystallization of the crude acid from acetone/tert.butyl methyl ether, 4.7 g of pure product of melting point 130° C.

$^1$H-NMR (DMSO-d$_6$): δ=1.13 (s, 9H, tBu), 1.38 (d, J=13 Hz, 3H, P-Me), 2.7–3.4 (m, 2H, 4-H), 4.1–4.6 (mc, 1H, 5-H), 9.75 ppm (sb, 1H, P-OH).

$C_8H_{16}NO_3P \times 0.2\ H_2O$ (208.8)

Analysis: Calc.: H$_2$O 1.72, C 46.02, H 7.92, N 6.71. Found: H$_2$O 1.7, C 46.02, H 7.63, N 6.91.

EXAMPLE 65

3-(4-Fluorophenyl)-2-isoxazolin-5-ylphosphonate

In analogy to Example 1, 23.6 g of product are obtained from 19.2 g (0.138 mol) of 4-fluorobenzaldoxime, 20.3 g (0.152 mol) of N-chlorosuccinimide, 18.8 g (0.138 mol) of dimethyl vinylphosphonate and 21.2 ml (0.152 mol) of triethylamine after recrystallization from tert-.butyl methyl ether (melting point: 94° C).

$^1$H-NMR (DMSO-d$_6$): δ=3.2–4.1 (m, 8H, 4-H and P(OMe)$_2$ as d, J=11 Hz, at 3.7 ppm), 4.8–5.25 (mc, 1H, 5-H), 7.0–7.9 ppm (m, 4H, Aryl-H).

$C_{11}H_{13}FNO_4P$ (273.2)

Analysis: Calc.: C 48.36, H 4.80, N 5.13. Found: C 48.24, H 4.64, N 5.31.

EXAMPLE 66

Dimethyl 3-(4-methoxycarbonylphenyl)-2-isoxazolin-5-ylphosphonate

Reaction of 80.6 g (0.45 mol) of methyl 4-hydroxyaminobenzoate, 67.0 g (0.5 mol) of N-chlorosuccinimide, 61.25 g (0.45 mol) of dimethyl vinylphosphonate and 78.45 ml (0.56 mol) of triethylamine as in Example 1 provides, after recrystallization from tert.butyl methyl ether, 115.2 g of pure product of melting point 93° C.

$^1$H-NMR (CDCl$_3$): δ=3.15–4.1 (m, 11H, 4-H, P(O-Me)$_2$ at 3.85 ppm and CO$_2$Me at 3.95 ppm), 4.7–5.2 (mc, 1H, 5-H), 7.75 and 8.1 ppm (AA'BB', 4H, Aryl-H).

$C_{13}H_{16}NO_6P$ (313.2)

Analysis: Calc.: C 49.85, H 5.15, N 4.47. Found: C 49.81, H 5.02, N 4.52.

EXAMPLE 67

3-(4-Fluorophenyl)-2-isoxazolin-5-ylphosphonic acid (by procedure (c))

14 g (51 mmol) of the dimethyl ester from Example 65 are converted as described in Example 34 into the phosphonic acid, and the latter is crystallized from dichloromethane. 11 g of product of melting point 206° C. are obtained.

$^1$H-NMR(DMSO-d$_6$): δ=3.0–3.85 (m, 2H, 4-H), 4.3–4.8 (mc, 1H, 5-H), 6.8–7.6 (m, 4H, Aryl-H), 10.7 ppm (sb, 2H, P(OH)$_2$).

$C_9H_9FNO_4P$ (245.2)

Analysis: Calc.: C 44.10, H 3.70, N 5.71. Found: C 43.69, H 3.53, N 5.79.

EXAMPLE 68

Dimethyl 3(4-nitrophenyl)-2-isoxazolin-5-ylphosphonate (by procedure (a))

Preparation is carried out in analogy to Example 1 from 19.6 g (0.118 mol) of 4-nitrobenzaldoxime, 17.4 g (0.13 mol) of N-chlorosuccinimide, 16.1 g (0.118 mol) of dimethyl vinylphosphonate and 18.7 ml (0.13 mol) of triethylamine. Crystallization of the crude product from tert.butyl methyl ether provides analytically pure compound of melting point 156° to 158° C.

$C_{11}H_{13}N_2O_6P$ (300.3)

$^1$H-NMR (DMSO-d$_6$): δ=3.1–4.05 (m, 8H, 4-H and P(OMe)$_2$ at 3.67 ppm), 4.8–5.3 (mc, 1H, 5-H), 7.83 and 8.15 ppm (AA'BB', 4H, Aryl-H).

EXAMPLE 69

3-(4-Nitrophenyl)-2-isoxazolin-5-ylphosphonic acid (by procedure (c))

7.0 g of the ester from Example 68 are cleaved as in Example 34 to give the phosphonic acid, which is crystallized from dichloromethane, resulting in 5.2 g of pure product of melting point 194° to 197° C. (decomposition).

$^1$H-NMR (DMSO-d$_6$): δ=2.8–3.85 (m, 2H, 4-H), 4.35–4.85 (mc, 1H, 5-H), 7.6 and 7.95 (AA'BB', 4H, aryl-H), 10.5 ppm (sb, 2H, P(OH)$_2$).

$C_9H_9N_2O_6P$ (272.2)

Analysis: Calc.: C 39.72, H 3.33, N 10.29. Found: C 39.55, H 3.02, N 10.19.

EXAMPLE 70

Dimethyl 3-(4-dimethylaminophenyl)-2-isoxazolin-5-ylphosphonate (by procedure (a))

In analogy to Example 1, 40 g (0.24 mol) of 4-dimethylaminobenzaldoxime, 36.17 g (0.27 mol) of N-chlorosuccinimide, 32.7 g (0.24 mol) of dimethyl vinylphosphonate and 52.3 ml (0.376 mol) of triethylamine are reacted. The resulting oily crude product is purified by chromatography on silica gel and recrystallization from tert.butyl methyl ether. 33.4 g of the isoxazoline of melting point 123° C. (decomposition) are obtained.

$C_{13}H_{19}N_2O_4P$ (298.3)

$^1$H-NMR (DMSO-d$_6$): $\delta = 2.8-3.85$ (m, 14H, 4-H, NMe$_2$ as s at 2.85 ppm and P(OMe)$_2$ as d, J = 10 Hz, at 3.6 ppm), 4.5–5.05 (mc, 1H, 5-H), 6.5 and 7.3 ppm (AA'BB', 4H, Aryl-H).

EXAMPLE 71

3-(4-Dimethylaminophenyl)-2-isoxazolin-5-ylphosphonic acid hydrobromide (by procedure (c))

10 g (33.5 mmol) of the ester from Example 70 are cleaved in accordance with Example 34 to give the phosphonic acid, and the latter is converted in methanol into 18.7 g of crystalline hydrobromide of melting point 214° C. (decomposition). On extensive drying under reduced pressure, the product loses about 20% hydrogen bromide.

$^1$H-NMR (DMSO-d$_6$): $\delta = 2.8-3.8$ (m, 8H, 4-H and NMe$_2$ as sb at 3.05 ppm), 4.4–4.9 (mc, 1H, 5-H), 7.15–7.65 (AA'BB', 4H, Aryl-H), 11.0 ppm (sb, ~3H, acidic H).

$C_{11}H_{15}N_2O_4P \times 0.8$ HBr (334.9)

Analysis: Calc.: C 39.44, H 4.76, N 8.36, Br 19.08. Found: C 39.34, H 4.64, N 8.37, Br 18.53.

EXAMPLE 72

Dimethyl 3-(2-hydroxyphenyl)-2-isoxazolin-5-ylphosphonate (by procedure (a))

41.1 g (0.3 mol) of salicylaldoxime in dichloromethane are refluxed with 40.1 g (0.3 mol) of N-chlorosuccinimide and 1.5 ml of pyridine for 3 hours. Ice-water is added and the mixture is extracted, and the hydroxamoyl chloride is recrystallized from dichloromethane/petroleum ether. 25.5 g (0.15 mol) of this are reacted with 20.4 g (0.15 mol) of dimethyl vinylphosphonate and 22.9 ml (0.165 mol) of triethylamine in dichloromethane in analogy to Example 5 to give 25.8 g of oily product.

$C_{11}H_{14}NO_5P$ (271.3)

$^1$H-NMR (CDCl$_3$): $\delta = 3.35-4.05$ (m, 8H, 4-H and P(OMe)$_2$ at 3.85 ppm), 4.6–5.1 (mc, 1H, 5-H), 6.7–7.55 (m, 4H, Aryl-H), 9.5 ppm (sb, 1H, OH).

EXAMPLE 73

3-(2-Hydroxyphenyl)-2-isoxazolin-5-ylphosphonic acid (by procedure (c))

20 g of the dimethyl ester from Example 72 are converted as in Example 34 into the phosphonic acid, which is recrystallized from dichloromethane (9.5 g, melting point 111° to 116° C. (decomposition)).

$^1$H-NMR (DMSO-d$_6$): $\delta = 3.1-3.95$ (m, 2H, 4-H), 4.35–4.9 (mc, 1H, 5-H), 6.7–8.5 ppm (m, ~7H, Aryl-H and acidic H).

$C_9H_{10}NO_5P$ (243.2)

Analysis: Calc.: C 44.46, H 4.15, N 5.76. Found: C 44.14, H 3.98, N 5.65.

EXAMPLE 74

Dimethyl 3-(2-thienyl)-2-isoxazolin-5-ylphosphonate (by procedure (a))

12.03 g (0.094 mol) of 2-thiophenecarbaldoxime are suspended in dichloromethane, and 11.23 g (0.103 mol) of tert.butyl hypochlorite dissolved in dichloromethane are added dropwise. The conversion to the hydroxamoyl chloride takes place in an exothermic reaction. After 3 hours, 14.1 g (0.103 ml) of dimethyl vinylphosphonate, and then, within 15 hours, 15.7 ml (0.113 mol) of triethylamine dissolved in dichloromethane, are added dropwise. Working up in analogy to Example 1 provides 19 g of oily crude product which is purified by chromatography on silica gel. 16.8 g of pure ester are obtained.

$C_9H_{12}NO_4PS$ (261.3)

$^1$H-NMR (CDCl$_3$): $\delta = 3.3-4.0$ (m, 8H, 4-H and P(OMe)$_2$ at 3.85 ppm, 4.65–5.1 (mc, 1H, 5-H), 6.8–7.55 ppm (m, 3H, Thienyl-H).

EXAMPLE 75

3-(2-Thienyl)-2-isoxazolin-5-ylphosphonic acid (by procedure (c))

4.5 g of crystalline phosphonic acid of melting point 169° C. (decomposition) are obtained from 8.9 g of the ester from Example 74 in analogy to Example 34 and recrystallization from dichloromethane.

$^1$H-NMR (DMSO-d$_6$): $\delta = 3.05-3.9$ (m, 2H, 4-H), 4.45–4.95 (mc, 1H, 5-H), 7.0–7.8 (m, 3H, Thienyl-H), 9.5 ppm (sb, 2H, P(OH)$_2$).

$C_7H_8NO_4PS$ (233.2)

Analysis: Calc.: C 36.05, H 3.46, N 6.01, S 13.75. Found: C 35.87, H 3.11, N 5.66, S 13.78.

EXAMPLE 76

Diethyl 3-tert.butyl-5-isoxazolylphosphonate (by procedure (b))

Preparation is carried out as described in Example 18 by reaction of 20.2 g (0.2 mol) of pivalaldoxime, 29.35 g (0.22 mol) of N-chlorosuccinimide, 53.5 g (0.22 mol) of diethyl α-bromovinylphosphonate and 61.2 ml (0.44 mol) of triethylamine in dichloromethane. The crude product which results as an oil is purified by chromatography on silica gel. 20.6 g of pure oily compound are obtained.

$^1$H-NMR (CDCl$_3$): $\delta = 1.0-1.5$ (15H, P(OEt)$_2$ and tBu as s at 1.33 ppm), 3.8–4.4 (m, 4H, P(OEt)$_2$), 6.65 ppm (d, J = 1.8 Hz, 1H, 4-H).

EXAMPLE 77

Diammonium 3-tert.butyl-5-isoxazolylphosphonate (by procedure (c))

12 g (46 mmol) of the diethyl ester from Example 76 are subjected to ester cleavage as in Example 34. Conversion into the diammonium salt in analogy to Example 35 and crystallization from acetone result in 10.3 g of the crystalline product of melting point 185° to 190° C., which may lose up to 25% ammonia on extensive drying under reduced pressure.

$^1$H-NMR (D$_2$O): $\delta = 1.3$ (s, 9H, tBu), 6.4 ppm (d, J = 1.5 Hz, 1H, 4-H).

EXAMPLE 78

Ethyl 3-bromo-2-isoxazolin-5-ylmethyl(P-methyl)phosphinate (by procedure (a))

20 g (0.135 mol) of ethyl allyl(P-methyl)phosphinate are dissolved in 570 ml of ethyl acetate, 49.7 g (0.6 mol) of sodium bicarbonate in 115 ml of water are added and, while stirring vigorously, a solution of 40.6 g (0.2 mol) of dibromoformaldoxime in 115 ml of ethyl acetate is slowly added dropwise. The product is isolated in the form of an oil, 15 g from the ethyl acetate phase, and a further 19 g from the aqueous phase by extraction with dichloromethane at pH 2.

¹H-NMR (CDCl₃): δ=1.3 (t, J=7 Hz, 3H, P-OEt), 1.55 (d, J=14 Hz, 3H, P-Me), 1.9-2.4 (m, 2H, CH₂-P), 2.9-3.5 (m, 2H, 4-H), 3.65-4.3 (mc, 2H, P-OEt), 4.6-5.35 ppm (mc, 1H, 5-H).

EXAMPLE 79

3-Chloro-2-isoxazolin-5-ylmethyl(P-methyl)phosphinic acid (by procedure (f))

3.9 g (35 mmol) of chlorotrimethylsilane are added to a solution, prepared under argon as protective gas, of 9 g (33 mmol) of the ester from Example 78 in 100 ml of dry dichloromethane, the mixture is left to stand at room temperature for 4 days, water is added to opalescence, and the mixture is then stirred for 1 hour and concentrated. Recrystallization of the residue from ethyl acetate/petroleum ether results in 3.3 g of pure product of melting point 116° C.

¹H-NMR (DMSO-d₆): δ=1.35 (d, J=14 Hz, 3H, P-Me), 1.8-2.3 (m, 2H, CH₂-P), 2.75-3.65 (m, 2H, 4-H), 4.5-5.2 (mc, 1H, 5-H), 9.7 ppm (sb, 1H, P-OH).

C₅H₉ClNO₃P (197.6)

Analysis: Calc.: C 30.40, H 4.59, N 7.09, Cl 17.95. Found: C 29.93, H 4.45, N 7.12, Cl 17.20.

All the abovementioned compounds are compiled with their variable structural elements R¹, A, n, X and Y in formula I in Table 3 which follows.

TABLE 3

| Example | R¹ | A | n | X | Y |
|---|---|---|---|---|---|
| 1 | 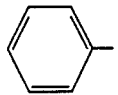 | —CH₂—CH— | 0 | —OC₂H₅ | —OC₂H₅ |
| 2 | 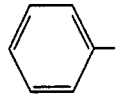 | —CH₂—CH— | 1 | —OC₂H₅ | —OC₂H₅ |
| 3 | 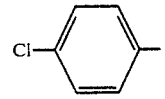 | —CH₂—CH— | 0 | —OC₂H₅ | —OC₂H₅ |
| 4 | 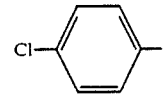 | —CH₂—CH— | 1 | —OC₂H₅ | —OC₂H₅ |
| 5 |  | —CH₂—CH— | 0 | —OCH₃ | —OCH₃ |
| 6 | 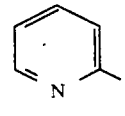 | —CH₂—CH— | 0 | —OC₂H₅ | —OC₂H₅ |
| 7 | 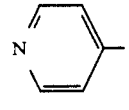 | —CH₂—CH— | 0 | —OC₂H₅ | —OC₂H₅ |
| 8 | 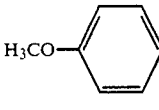 | —CH₂—CH— | 0 | —OC₂H₅ | —OC₂H₅ |
| 9 | 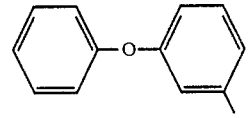 | —CH₂—CH— | 0 | —OCH₃ | —OCH₃ |
| 10 | 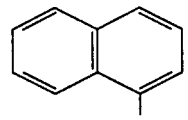 | —CH₂—CH— | 0 | —OCH₃ | —OCH₃ |

TABLE 3-continued

| | | Compounds of the formula I | | | |
|---|---|---|---|---|---|
| Example | R¹ | A | n | X | Y |
| 11 | phenyl-CH=CH- | -CH$_2$-CH- | 0 | -OC$_2$H$_5$ | -OC$_2$H$_5$ |
| 12 | phenyl-CO- | -CH$_2$-CH- | 0 | -OC$_2$H$_5$ | -OC$_2$H$_5$ |
| 13 | phenyl- | -CH$_2$-CH- | 0 | -CH$_3$ | -OCH$_3$ |
| 14 | 4-H$_3$CO-phenyl- | -CH$_2$-CH- | 0 | -CH$_3$ | -OCH$_3$ |
| 15 | 4-H$_3$C-phenyl- | -CH$_2$-CH- | 0 | -CH$_3$ | -OCH$_3$ |
| 16 | 1-naphthyl- | -CH$_2$-CH- | 0 | -CH$_3$ | -OCH$_3$ |
| 17 | phenyl- | -CH$_2$-CH- | 0 | -CH$_3$ | -CH$_3$ |
| 18 | phenyl- | -CH=C- | 0 | -OC$_2$H$_5$ | -OC$_2$H$_5$ |
| 19 | 4-H$_3$CO-phenyl- | -CH=C- | 0 | -OC$_2$H$_5$ | -OC$_2$H$_5$ |
| 20 | 2-pyridyl- | -CH=C- | 0 | -OC$_2$H$_5$ | -OC$_2$H$_5$ |
| 21 | 4-pyridyl- | -CH=C- | 0 | -OC$_2$H$_5$ | -OC$_2$H$_5$ |
| 22 | H$_3$C-(CH$_2$)$_2$- | -CH$_2$-CH- | 0 | -OC$_2$H$_5$ | -OC$_2$H$_5$ |
| 23 | phenyl-CH$_2$- | -CH$_2$-CH- | 0 | -OCH$_3$ | -OCH$_3$ |

TABLE 3-continued

| Example | R¹ | A | n | X | Y |
|---|---|---|---|---|---|
| 24 | C₆H₅—CH₂— | —CH₂—CH— | 0 | —CH₃ | —OCH₃ |
| 25 | (H₃C)₃C— | —CH₂—CH— | 0 | —CH₃ | —OCH₃ |
| 26 | (H₃C)₃C— | —CH₂—CH— | 0 | —OC₂H₅ | —OC₂H₅ |
| 27 | C₆H₅— | —CH₂—CH— | 0 | —OH | —OC₂H₅ |
| 28 | H₃CO—C₆H₄— | —CH₂—CH— | 0 | —O⁻NH₄⁺ | —OC₂H₅ |
| 29 | H₃CO—C₆H₄— | —CH₂—CH— | 0 | —CH₃ | —O⁻NH₄⁺ |
| 30 | CH₃—C₆H₄— | —CH₂—CH— | 0 | —CH₃ | —OH |
| 31 | C₆H₅—CH₂— | —CH₂—CH— | 0 | —CH₃ | —O⁻NH₄⁺ |
| 32 | naphthyl | —CH₂—CH— | 0 | —CH₃ | —OH |
| 33 | (H₃C)₃C— | —CH₂—CH— | 0 | —OH | —OH |
| 34 | C₆H₅— | —CH₂—CH— | 0 | —OH | —OH |
| 35 | C₆H₅— | —CH₂—CH— | 0 | —O⁻NH₄⁺ | —O⁻NH₄⁺ |
| 36 | C₆H₅— | —CH₂—CH— | 0 | —O⁻Na⁺ | —O⁻Na⁺ |
| 37 | C₆H₅— | —CH₂—CH— | 0 | —OH | —O⁻K⁺ |
| 38 | C₆H₅— | —CH₂—CH— | 0 | —OH | —OH | x 2 lysine

TABLE 3-continued
| | | Compounds of the formula I | | | |
|---|---|---|---|---|---|
| Example | R¹ | A | n | X | Y |
| 39 | 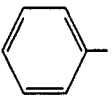 | —CH₂—CH— | 1 | —OH | —OH |
| 40 | 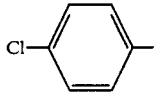 | —CH₂—CH— | 0 | —OH | —OH |
| 41 | 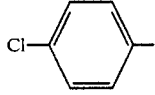 | —CH₂—CH— | 1 | —OH | —OH |
| 42 | 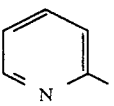 x HBr | —CH₂—CH— | 0 | —OH | —OH |
| 43 | 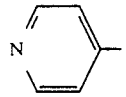 | —CH₂—CH— | 0 | —O⁻NH₄⁺ | —O⁻NH₄⁺ |
| 44 | 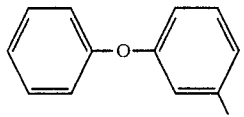 | —CH₂—CH— | 0 | —OH | —OH |
| 45 | 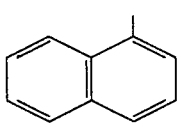 | —CH₂—CH— | 0 | —OH | —OH |
| 46 | 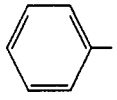 | —CH=C— | 0 | —OH | —OH |
| 47 | H₃C—(CH₂)₂— | —CH₂—CH— | 0 | —O⁻NH₄⁺ | —O⁻NH₄⁺ |
| 48 | 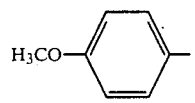 | —CH₂—CH— | 0 | —OH | —OH |
| 49 | 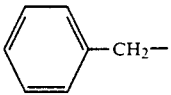 | —CH₂—CH— | 0 | —OH | —OH |
| 50 | 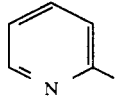 | —CH=C— | 0 | —O⁻NH₄⁺ | —O⁻NH₄⁺ |
| 51 | 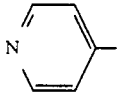 | —CH=C— | 0 | —O⁻NH₄⁺ | —O⁻NH₄⁺ |

TABLE 3-continued

Compounds of the formula I

| Example | R¹ | A | n | X | Y |
|---|---|---|---|---|---|
| 52 | styryl (Ph—CH=CH—) | —CH$_2$—CH— | 0 | —OH | —OH |
| 53 | benzoyl (Ph—CO—) | —CH$_2$—CH— | 0 | —O$^-$NH$_4^+$ | —O$^-$NH$_4^+$ |
| 54 | 4-methoxyphenyl (H$_3$CO—C$_6$H$_4$—) | —CH=C— | 0 | —O$^-$NH$_4^+$ | —O$^-$NH$_4^+$ |
| 55 | phenyl | —CH$_2$—CH— | 0 | —OC$_2$H$_5$ | pyrrolidin-1-yl (—N⟨(CH$_2$)$_4$⟩) |
| 56 | phenyl | —CH$_2$—CH— | 0 | —OC$_2$H$_5$ | —NH—CH$_2$—C(O)—O—CH$_2$—C$_6$H$_5$ |
| 57/58 | phenyl | —CH$_2$—CH— | 0 | —CH$_3$ | —NH—CH$_2$—C(O)—O—CH$_2$—C$_6$H$_5$ |
| 59 | phenyl | —CH$_2$—CH— | 0 | —N(CH$_3$)$_2$ | —N(CH$_3$)$_2$ |
| 60a | phenyl (+)-Enantiomer | —CH$_2$—CH— | 0 | —OCH$_3$ | —OCH$_3$ |
| 60b | phenyl (−)-Enantiomer | —CH$_2$—CH— | 0 | —OCH$_3$ | —OCH$_3$ |
| 61 | phenyl (+)-Enantiomer | —CH$_2$—CH— | 0 | —OH | —OH |
| 62 | phenyl (−)-Enantiomer | —CH$_2$—CH— | 0 | —OH | —OH |

TABLE 3-continued

Compounds of the formula I

| Example | R¹ | A | n | X | Y |
|---|---|---|---|---|---|
| 63 | phenyl | —CH₂—CH— | 0 | —CH₃ | —OH |
| 64 | (H₃C)₃C— | —CH₂—CH— | 0 | —CH₃ | —OH |
| 65 | 4-F-phenyl | —CH₂—CH— | 0 | —OCH₃ | —OCH₃ |
| 66 | 4-(H₃CO-CO)-phenyl | —CH₂—CH— | 0 | —OCH₃ | —OCH₃ |
| 67 | 4-F-phenyl | —CH₂—CH— | 0 | —OH | —OH |
| 68 | 4-O₂N-phenyl | —CH₂—CH— | 0 | —OCH₃ | —OCH₃ |
| 69 | 4-O₂N-phenyl | —CH₂—CH— | 0 | —OH | —OH |
| 70 | 4-(H₃C)₂N-phenyl | —CH₂—CH— | 0 | —OCH₃ | —OCH₃ |
| 71 | 4-(H₃C)₂N-phenyl × HBr | —CH₂—CH— | 0 | —OH | —OH |
| 72 | 2-OH-phenyl | —CH₂—CH— | 0 | —OCH₃ | —OCH₃ |
| 73 | 2-OH-phenyl | —CH₂—CH— | 0 | —OH | —OH |
| 74 | 2-thienyl | —CH₂—CH— | 0 | —OCH₃ | —OCH₃ |
| 75 | 2-thienyl | —CH₂—CH— | 0 | —OH | —OH |
| 76 | (H₃C)₃C— | —CH=C— | 0 | —OC₂H₅ | —OC₂H₅ |
| 77 | (H₃C)₃C— | —CH=C— | 0 | —O⁻NH₄⁺ | —O⁻NH₄⁺ |
| 78 | Br | —CH₂—CH— | 1 | —CH₃ | —OC₂H₅ |

TABLE 3-continued

| | | Compounds of the formula I | | | |
|---|---|---|---|---|---|
| Example | R¹ | A | n | X | Y |
| 79 | Cl | —CH₂—CH— | 1 | —CH₃ | —OH |

The other Examples 80–105 which follow were carried out in analogy to the examples described above (cycloaddition of the appropriate aliphatic and aromatic nitrile oxides onto olefinic phosphorus compounds and, where appropriate, transformation of the functional groups). The resulting compounds of the formula I were identified by elemental analyses and nuclear magnetic resonance spectra; the compounds are compiled in Table 3a in the same manner as the compounds of Examples 1–79 above, with the melting points also being included in the table in this case.

Supplementary notes to some Examples are given in the footnotes to Table 3a.

TABLE 3a

| | | Compounds of the formula I | | | | |
|---|---|---|---|---|---|---|
| Example | R¹ | A | n | X | Y | Melting point (°C.) |
| 80 | 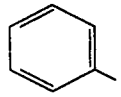 | —CH₂—CH— | 0 | —OH | —OCH₃ | 141–144 |
| 81 | 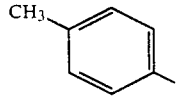 | " | 0 | —OH | —OH | 218 |
| 82 | 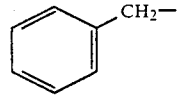 | " | 1 | —OH | —OH | 110–119 |
| 83 | 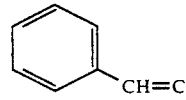 | " | 1 | —OH | —OH | 230–234 (decomp.) |
| 84⁽¹⁾ | 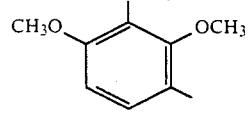 | " | 0 | —O⁻Na⁺ | —O⁻Na⁺ | >280 |
| 85 | 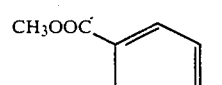 | " | 0 | —OH | —OH | 218 (decomp.) |
| 86 | 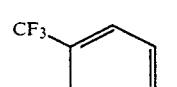 | " | 0 | —OH | —OH | 195–197 |
| 87⁽²⁾ | 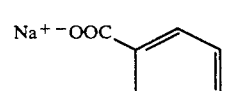 | —CH₂—CH— | 0 | —O⁻Na⁺ | —O⁻Na⁺ | >295 |
| 88⁽³⁾ | 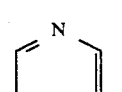 | " | 0 | —OH | —OH | 271 (decomp.) |
| 89⁽⁴⁾ | 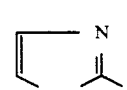 | " | 0 | —OH | —OH | 179–188 (decomp.) |

TABLE 3a-continued

Compounds of the formula I

| Example | R¹ | A | n | X | Y | Melting point (°C.) |
|---|---|---|---|---|---|---|
| 90[5] | (CH₃)₂C(OH)– | " | 0 | –OCH₃ | –OCH₃ | Oil |
| 91[6] | HOOC– | " | 1 | –OC₂H₅ | –OC₂H₅ | 111 |
| 92[7] | HOOC– | " | 1 | –OH | –OC₂H₅ | 124 |
| 93 | (H₃C)₃C– | " | 1 | –O⁻NH₄⁺ | –O⁻NH₄⁺ | >180 (decomp.) |
| 94[8] | phenyl– | " | 0 | –O–(CH₂)₃–O– | | 152 |
| 95 | (2-pyridyl)– | –CH₂–CH– | 0 | –CH₃ | –OH | 138–139 |
| 96[9] | 4-(CH₃OOC)–C₆H₄– | " | 0 | –CH₃ | –OH | 214–216 (decomp.) |
| 97[10] | 4-(HOOC)–C₆H₄– | " | 0 | –CH₃ | –OH | 259–261 (decomp.) |
| 98[11] | phenyl– | " | 1 | –CH₃ | –OH | 147 |
| 99[12] | (CH₃)₃C– | " | 1 | –CH₃ | –O⁻NH₄⁺ | 161–165 |
| 100 | (2-thienyl)– | " | 0 | –CH₃ | –OH | 151–158 |
| 101[13] | C₂H₅OOC– | –CH₂–CH– | 0 | –CH₃ | –OH | 96 (decomp.) |
| 102[14] | Na⁺⁻OOC– | " | 0 | –CH₃ | –O⁻Na⁺ | 210–215 (decomp.) |
| 103[15] | 4-(H₂N–CO)–C₆H₄– | " | 0 | –CH₃ | –OH | 261 (decomp.) |
| 104[16] | C₆H₅–CH₂– | –CH=C– | 0 | –O⁻NH₄⁺ | –O⁻NH₄⁺ | 197–203 (decomp.) |

TABLE 3a-continued

Compounds of the formula I

| Example | R¹ | A | n | X | Y | Melting point (°C.) |
|---|---|---|---|---|---|---|
| 105[17] | 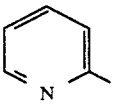 | —CH₂—CH— | 0 | —CH₃ | —CH₃ | 185 |

Footnotes to Table 3a
[1] Precipitation from methanolic solution using sodium 2-ethylhexanoate
[2] Prepared by alkaline hydrolysis of the compound from Example 85
[3] Prepared from 3-pyridylhydroxamoyl chloride hydrochloride in analogy to Examples 6 and 42
[4] Prepared from 2-thiazolecarbaldoxime (cf. A. Dondoni et al., Synthesis 1987, 998) in analogy to Examples 2 and 34
[5] Synthesized starting from 2-trimethylsilyloxy-2-methyl-1-nitropropane (cf. D. P. Curran et al., J. Org. Chem. 49 (1984), 3474) in analogy to Example 22; elimination of the protective group using trifluoroacetic acid
[6] The nitrile oxide is generated from ethyl chloroxyiminoacetate using triethylamine in analogy to Example 1; the corresponding ethyl isoxazolin-3-carboxylate is hydrolyzed with 1 equivalent of sodium hydroxide solution, then crystallized as acid
[7] From Example 91 with excess of sodium hydroxide solution
[8] Prepared in analogy to Example 56: activation with 2 equivalents of PCl₅, then reaction with 1,3-propanediol and triethylamine
[9] Selective cleavage of the ethyl phosphinate using HBr/glacial acetic acid
[10] From Example 96 by alkaline hydrolysis
[11] Procedure in analogy to Examples 1 and 33; ethyl allyl(P-methyl)phosphinate was used as olefin component
[12] In analogy to Example 98
[13] For preparation, see Example 91; the phosphinic ester was cleaved using HBr/glacial acetic acid
[14] From Example 101 by alkaline hydrolysis
[15] Introduction of the carbamoyl substituent by treating the appropriate nitrile with hydrogen bromide
[16] In analogy to Examples 18 and 23
[17] In analogy to Example 17

Pharmacological tests and results

To characterize the valuable immunomodulating properties and excellent tolerability of the compounds of the formula I they were investigated in experimental test systems which are recognized as being especially suitable for assessing the type of action of products having immunopharmacological activity.

1. Active Arthus reaction in the rat

The experimental animals used were female and male Sprague-Dawley rats with a body weight between 80 and 100 g which received subcutaneous injections into the tail-head of 0.5 ml of an emulsion of pertussis vaccine and ovalbumin in liquid paraffin. After two weeks, the rats were divided into groups each of 8 animals. 24 hours and 1 hour before induction of the Arthus reaction by injection of 0.1 ml of a 0.4% strength ovalbumin solution into the right hind paw, the particular test substance or the pure vehicle (positive control) was administered orally, sodium chloride solution was injected into the left paw. One group of unsensitized animals (negative control group) was likewise treated with ovalbumin in order to be able to rule out nonspecific reactions to the protein. The parameter used for measuring the action of the product was the percentage change in the increase in paw volume compared with that in the control group which was sensitized but untreated (positive control) 4 hours after ovalbumin challenge, when the swelling had reached its maximum.

2. Acute toxicity

The LD₅₀ values were determined by the standard method via the mortality occurring within 7 days in NMRI (Naval Medical Research Institute) mice (6 animals per dose) after a single intraperitoneal (i.p.) or intravenous (i.v.) dose.

The results of the experiments on the Arthus reaction and toxicity are compiled in Table 4 which follows.

TABLE 4

Effect on the active Arthus reaction and acute toxicity

| Compound from Example | Active Arthus Oral dose in mg/kg | reaction % change | Acute toxicity LD₅₀ (mg/kg) i.p. | i.v. |
|---|---|---|---|---|
| 5 | 100 | −20 | 300–600 | |
| 13 | 50 | −13 | | >200 |
| 17 | 35 | −34 | | >200 |
| 27 | 70 | +108 | | >200 |
| 28 | 25 | −12 | | >200 |
| 31 | 50 | +66 | | >200 |
| 32 | 50 | +42 | 600–1200 | |
| 33 | 100 | −15 | | >200 |
| 34 | 35 | −16 | 200–300 | |
| 35 | 35 | −16 | | >200 |
| 39 | 50 | +24 | 600–1200 | |
| 40 | 50 | −23 | | >200 |
| 41 | 100 | +26 | 150–300 | |
| 42 | 35 | −33 | | >200 |
| 43 | 50 | −14 | | >200 |
| 45 | 50 | −25 | 75–150 | |
| 46 | 50 | −36 | | >200 |
| 47 | 25 | −35 | | >200 |
| 48 | 100 | +10 | 300–600 | |
| 49 | 50 | −59 | | >200 |
| 50 | 25 | −18 | | >200 |
| 51 | 50 | +17 | | >200 |
| 52 | 50 | −15 | | |
| 54 | 40 | −57 | | >200 |
| 55 | 70 | −23 | | >200 |
| 56 | 100 | +35 | >1200 | |
| 57/58 | 12 | +22 | | 50–100 |
| 59 | 50 | −25 | | >200 |
| 61 | 50 | +52 | | |
| 62 | 50 | +16 | | |
| 63 | 50 | −48 | 300–600 | |
| 64 | 20 | −59 | | >200 |
| 65 | 25 | −25 | >300 | |
| 66 | 50 | −28 | | |
| 67 | 50 | −35 | | |
| 69 | 50 | −20 | | >100 |
| 71 | 70 | −10 | 150–300 | |
| 73 | 35 | −44 | 150–300 | |
| 75 | 35 | −26 | | >100 |
| 77 | 35 | −20 | | |
| 79 | 70 | −24 | | |
| 87 | 35 | −29 | | |
| 88 | 50 | −50 | | |
| 90 | 50 | −31 | | |
| 99 | 35 | −32 | | >100 |
| 101 | 70 | −32 | | >100 |

TABLE 4-continued

Effect on the active Arthus reaction and acute toxicity

| Compound from Example | Active Arthus Oral dose in mg/kg | reaction % change | Acute toxicity LD$_{50}$ (mg/kg) i.p. | i.v. |
|---|---|---|---|---|
| 102 | 35 | −35 | | |
| 105 | 35 | −23 | | >100 |

3. Chronic graft-versus-host (cGvH) reaction in the mouse

Graft-versus-host disease, which derives from an immune reaction originating from the transplant and directed against the host tissue, is characterized, in the acute form which almost always has a fatal outcome, by enlargement of the spleen, swelling of the liver, hypertrophy of the lymph nodes, hemolytic anemia, lowered immunoglobulin and complement levels and diminished immunoreactivity. The chronic form of the disease, which has a somewhat milder course, leads to lymphadenopathy, immune complex glomerulonephritis and excessive formation of non-organ-specific autoantibodies. A syndrome with similar features is systemic lupus erythematosus (SLE) which is likewise one of the autoimmune diseases.

The investigation of the compounds used according to the invention for the progress of the cGvH reaction induced in female mice of (DBA/2×C57Bl/6)F1 generation by two injections of spleen and thymus cells mixed together are carried out in the experimental system described by S. Popovic and R. R. Bartlett (Agents and Actions 21 (1987), 284–286), with $5 \times 10^7$ DBA/2 cells, likewise obtained from female donor animals, being administered intravenously in 0.2 ml of culture medium each time at a time interval of 7 days. For a reliable assessment of the outbreak and course of the disease, a group of healthy animals was included as negative control in all experiments. The 6-week oral treatment of the animals with the disease started on day 21 after the first donor cell injection, with the test substances or the pure vehicle (positive control) being administered once a day. The vehicle used was an aqueous CMC (carboxymethylcellulose sodium salt) solution containing 100 mg of CMC per 1. The volume administered was 10 ml per kg body weight. The individual experimental groups each comprised 10 animals.

The action of the products was assessed on the basis of the inhibition of proteinuria and the cGvH index. As a consequence of the destruction of nephrons by deposition of immune complexes on the basement membranes of the glomeruli, the animals with the disease developed pronounced proteinuria, which correlates with the extent of glomerulonephritis and can easily be quantified via the increase in the amount of protein excreted with the urine. The second parameter measured, the cGvH index, relates to the great enlargement of the spleen (splenomegaly) caused by the cGvH reaction. It is defined as the quotient of the product of the spleen and body weights of the animals with the disease and of the product of the corresponding weights of healthy untreated animals on the negative control group, and is a reliable measure of the intensity of the disease (the greater this index, the more severe the disease).

The results of these investigations which are compiled in Table 5 demonstrate that compounds of the formula I are able to alleviate effectively cGvH disease by intervening to modulate the autoimmune processes.

TABLE 5

Inhibition of proteinuria and the cGvH index

| Compound from Example | Oral dose in mg/kg/day | % inhibition Proteinuria | cGvH index |
|---|---|---|---|
| 54 | 15 | 27 | 16 |
|  | 50 | 64 | 18 |
| 63 | 15 | 76 | 54 |
|  | 30 | 61 | 48 |

4. Inhibiting action on the activity of aminopeptidase enzymes

The activity of the enzyme aminopeptidase B was determined photometrically using the substrate L-lysine 2-naphthylamide at room temperature. Addition of the test substances in concentrations of 0.1–100 μg/ml to the enzyme mixture resulted in a dose-dependent suppression of enzyme activity. These data were used to calculate the concentrations of substance which bring about a 50% inhibition of enzyme activity (IC$_{50}$). In the same way, the inhibition of leucine aminopeptidase was investigated using L-leucine 4-nitroanilide as enzyme substrate. The IC$_{50}$ values are compiled in Table 6.

TABLE 6

Inhibition of aminopeptidases

| Compound from Example | Aminopeptidase B IC$_{50}$ (μg/ml) | Leucine aminopeptidase IC$_{50}$ (μug/ml) |
|---|---|---|
| 1 | | 65 |
| 13 | 100 | |
| 34 | 22.5 | 24 |
| 35 | | 57 |
| 36 | | 56 |
| 37 | | 52 |
| 45 | | 92 |
| 47 | | 35 |
| 48 | | 100 |
| 53 | | 65 |
| 61 | | 26 |
| 62 | | 130 |
| 67 | | 57 |
| 69 | | 27 |
| 71 | | 37 |
| 75 | | 79 |

5. Action on the delayed-type cellular immune reaction to sheep erythrocytes [DTH(delayed-type hypersensitivity) reaction]

Groups each comprising 5 female NMRI mice with a body weight of 18 to 20 g were formed, and each animal was given $10^6$ or $10^9$ sheep red blood cells intravenously. Sheep erythrocytes are regarded in immunology as a standard antigen with which it is possible to check cellular and humoral immunoreactivity, especially the functioning of the T-cell-dependent component of the immune system, the so-called T-helper cells. The test substances were administered, in intraperitoneal doses of 5 to 100 mg/kg in physiological saline, at the same time as the antigen. After 5 days, each animal was given an injection of $2 \times 10^8$ sheep erythrocytes into the footpad. 24 hours later, the swelling of the foot was measured. The foot swelling is induced by a skin reaction of the delayed type (DTH reaction) and, as is known to those skilled in the art, is a measure of the cellular immune response (J. Immunol. 101 (1968), 830-845). The test results obtained with the product of Example 34, by way of example, are compiled in Table 7 and illustrate that the compounds of the formula I—administered prophylactically—are able to increase the cellular immune response after immunization with the antigen by stimulation of the T-cell system, with the stimulant action reaching its optimum in this experiment at a dose of 25 mg/kg.

Table 8 shows the relative action of other test substances at a dose of 40 mg/kg relative to that of the compound of Example 34, whose maximal stimulation (difference between treated and untreated animals) corresponds to 100%.

6. Stimulation of non-specific immunity—activation of mononuclear phagocytes Macrophages play a central part in all immune processes, including the defenses against infective agents. On the one hand, they themselves are involved in the elimination of the pathogens and, on the other hand, they exert control functions in regulating the humoral (B-cell-dependent) and the cellular (T-cell-dependent) immune systems. In this case, the stimulant effect on peritoneal macrophages by the compounds used according to the invention was investigated in female NMRI mice 6 to 8 weeks old. The animals received the test substances in doses of 5, 10, 20 and 40 mg/kg parenterally or orally. The animals in the control group received physiological saline. Three days after administration of the substance, the peritoneal macrophages of the animals were examined for their state of activation on the basis of the secretion of lysosomal enzymes and the chemiluminescence as a measure of the oxidative metabolic capacity. For this purpose, either $3 \times 10^6$ macrophages were cultivated with 1 ml of TC 199 culture medium in Petri dishes with a diameter of 3 cm, or else $10^6$ macrophages were cultivated with 0.1 ml of culture medium in roundbottomed polyethylene tubes, at 37° C. under an atmosphere with a $CO_2$ content of 5%. After incubation for one hour, the cultures were washed in order to remove floating cells. The tube cultures were then used to determine the chemiluminescence with the aid of a Biolumate. The cell cultures in the Petri dishes were again incubated at 37° C. for 24 hours and subsequently used to determine the activity of the lysosomal enzymes liberated by exocytosis.

TABLE 7

| | Effect on the cellular immune response (DTH reaction) | | |
|---|---|---|---|
| Test substance | Dose in mg/kg (1x i.p.) | % Foot swelling after immunization with | |
| | | $10^6$ erythrocytes | $10^9$ erythrocytes |
| PBS* (vehicle) | | 15.6 ± 4.1 | 16.9 ± 4.0 |
| Compound from Example 34 | 5.0 | 25.3 ± 5.8 | 22.8 ± 3.5 |
| | 10.0 | 28.9 ± 7.7 | 24.1 ± 5.7 |
| | 12.5 | 29.9 ± 3.5 | 26.1 ± 8.9 |
| | 20.0 | 32.5 ± 3.0 | 30.5 ± 6.5 |
| | 25.0 | 33.7 ± 6.6 | 34.1 ± 7.4 |
| | 40.0 | 29.7 ± 4.7 | 32.8 ± 5.6 |
| | 50.0 | 29.2 ± 6.9 | 28.1 ± 4.1 |
| | 100.0 | 27.3 ± 4.6 | 26.6 ± 5.0 |

*PBS = phosphate-buffered saline (NaCl: 8 g/l, KCl: 0.2 g/l, $Na_2HPO_4 \cdot 2 H_2O$: 1.44 g/l, $KH_2PO_4$: 0.2 g/l)

TABLE 8

| Stimulation of the DTH reaction | |
|---|---|
| Compound from Example | Relative stimulation of the DTH reaction after a single i.p. dose of 40 mg/kg, in % |
| 34 | 100 |
| 27 | 94 |
| 30 | 76 |
| 35 | 98 |
| 36 | 102 |
| 37 | 77 |
| 39 | 136 |
| 53 | 68 |
| 61 | 108 |
| 62 | 83 |

It emerged from this that compounds of the formula I stimulate, both after intraperitoneal (i.p.) and after oral (p.o.) administration, macrophage activity and thus have an immunity-enhancing action. Thus, for example, with both modes of administration the compound of Example 34, which was tested widely for dose-finding, brought about a pronounced dose-dependent increase in chemiluminescence as a consequence of the activation of oxidative macrophage metabolism with increased formation of oxygen radicals and thus increased emission of light. It is evident from Table 10 that the macrophages of the control animals release only small amounts of lysosomal enzymes ($\beta$-glucuronidase ($\beta$-Glu), $\beta$-galactosidase ($\beta$-Gal) and N-acetyl-$\beta$-D-glucosaminidase (N-Ac-Glu)) into the culture supernatant. In contrast, the release of these acid hydrolases from the mononuclear phagocytes of the animals treated intraperitoneally or orally with, for example, the compound of Example 34 was increased as a function of the dose. Table 11 shows the relative effect of other test substances at an i.p. dose of 40 mg/kg relative to that of the compound of Example 34, whose maximum activation (difference between treated and untreated animals) corresponds to 100% in each case.

TABLE 9

| Effect on the oxidative metabolism of peritoneal macrophages of the mouse | | | |
|---|---|---|---|
| Test substance | Dose in mg/kg | Chemiluminescence in (RLU*/15 min) $\times 10^3$ after a single dose of product | |
| | | i.p. | p.o. |
| PBS (vehicle) | | 368 ± 31 | 359 ± 48 |
| Compound from Example 34 | 5 | 842 ± 42 | 728 ± 101 |
| | 10 | 2842 ± 223 | 2140 ± 156 |
| | 20 | 4935 ± 516 | 3286 ± 283 |
| | 40 | 6990 ± 290 | 4405 ± 197 |

*RLU = relative light units

TABLE 10

| Stimulation of the release of lysosomal enzymes from peritoneal macrophages of the mouse | | | | | | | |
|---|---|---|---|---|---|---|---|
| Test substance | Dose in mg/kg | Enzyme activity in mU/ml after a single dose of the product | | | | | |
| | | $\beta$-Glu | | $\beta$-Gal | | N-Ac-Glu | |
| | | i.p. | p.o. | i.p. | p.o. | i.p. | p.o. |
| PBS (vehicle) | | 751 | 678 | 1179 | 1051 | 1867 | 1701 |
| Compound from Example 34 | 5 | 1197 | 973 | 2357 | 2216 | 2607 | 2071 |
| | 10 | 1542 | 1393 | 3956 | 3513 | 4822 | 4283 |
| | 20 | 2067 | 1979 | 6918 | 6011 | 6812 | 6128 |
| | 40 | 2547 | 2286 | 9318 | 9262 | 9281 | 8432 |

TABLE 11

Stimulation of macrophage activity

| Compound from Example | Relative stimulation of macrophage activity in % after a single i.p. dose of 40 mg/kg | |
|---|---|---|
| | Chemiluminescence | Exocytosis |
| 34 | 100 | 100 |
| 5 | | 54 |
| 13 | 64 | 51 |
| 27 | 63 | 78 |
| 28 | 31 | 47 |
| 29 | | 38 |
| 35 | 107 | 113 |
| 36 | 88 | 99 |
| 37 | 97 | 104 |
| 39 | 42 | 86 |
| 40 | 38 | 29 |
| 41 | | 43 |
| 42 | 35 | 41 |
| 46 | 27 | 56 |
| 47 | 44 | 32 |
| 53 | 72 | 94 |
| 55 | 46 | 67 |
| 56 | | 43 |
| 60a | 51 | 88 |
| 60b | 24 | 63 |
| 61 | 76 | 81 |
| 62 | 94 | 96 |
| 67 | 56 | 72 |
| 69 | 49 | 84 |
| 71 | 37 | 35 |
| 79 | 44 | 57 |

The compounds of the formula I were additionally investigated in various experimental models of infection, this once again allowing impressive demonstration of their therapeutic potential based on the immunomodulating properties. Experimental results obtained with the compound of Example 34, by way of example, are described hereinafter.

7. Effect on the skin reaction of the delayed type (DTH reaction) in mice infected with Listeria monocytogenes In this experiment, the specific, cell-mediated immunity against the bacterium Listeria monocytogenes was investigated by means of the DTH reaction Female NMRI mice were infected with $2 \times 10^2$ live bacteria and then divided into groups each containing 10 animals. The treatment of the animals by intraperitoneal administration of the product in doses of 0.1, 1 or 10 mg/kg was started the same day. This treatment was repeated after 2, 4 and 6 days. Infected animals in a fourth experimental group, which received merely the pure vehicle i.p. in place of the product, acted as positive control. On day 13 of the experiment the DTH reaction was induced by injection of a soluble antigen obtained from Listeria monocytogenes into the footpad. 10 uninfected animals in a 5th experimental group (negative control) were likewise treated with the antigen in order to rule out non-specific reactions to the antigen challenge 24 hours after the administration of antigen, the percentage increase in the paw volume was determined as a measure of the induced DTH reaction. The experimental results compiled in Table 12 show that the increase in the DTH reaction, and thus in the cell-mediated immunity, by the test substance is dose-dependent, and, above doses of 1 mg/kg, significant.

TABLE 12

Effect on the DTH reaction to Listeria monocytogenes

| Experimental group | Dose in mg/kg (4 × i.p.) | DTH reaction % increase in the paw volume |
|---|---|---|
| Negative control | | 0.8 ± 1.8 |
| Positive control | | 9.8 ± 6.4 |
| Active product groups (treated with compound from Example 34) | 0.1 | 13.3 ± 9.7 |
| | 1.0 | 15.0 ± 7.0 |
| | 10.0 | 19.2 ± 9.4* |

*Significance p <0.05 (Student's t-test)

The same experimental system was also used to examine the effect of the test substance on i.p. administration of 10 mg/kg on the DTH reaction of female NMRI mice after infection with differing amounts of the bacterium Listeria monocytogenes. The animals received either $2 \times 10^2$ or $5 \times 10^2$ organisms. The results are shown in Table 13. According to this, although the DTH reaction is increased by the test substance at both organism concentrations, this stimulation is distinctly more pronounced in the animal group infected with the lower number of organisms.

TABLE 13

Effect on the DTH reaction with mice infected with Listeria monocytogenes

| Number of organisms administered | Experimental group | DTH reaction % increase in the paw volume |
|---|---|---|
| $2 \times 10^2$ | Positive control | 11.3 ± 15.3 |
| | Active product group* | 30.9 ± 15.3 |
| $5 \times 10^2$ | Positive control | 12.3 ± 11.5 |
| | Active product group* | 17.9 ± 12.1 |

*4 × 10 mg/kg i.p. (Compound from Example 34)

8. Effect on mortality and organ colonization in mice infected with Listeria monocytogenes Female NMRI mice (10 animals/group) were infected with a low dose of Listeria monocytogenes ($2 \times 10^2$). This dose is sublethal for the animals, i.e. they do not die from the infection but develop, as described in the previous experiment, a specific cell-mediated immunity which is enhanced by the compounds of the formula I. The investigation now was of how this effect operates on the progress of the disease after a second exposure to $10^6$ organisms of the bacterium *Listeria monocytogenes* carried out 15 days after the first infection. As is evident from Table 14, 4 of the 10 animals in the control group died, and all 6 surviving animals (100%) showed colonization of the liver with Listeria monocytogenes 5 days after the second infection. In contrast, all 10 animals in the active product group, where the animals had received the compound of Example 34 in the treatment regimen of the experiment described above (4 × 10 mg/kg i.p.) after the first infection, survived the second infection, and organisms were detectable in the liver of only 2 of them (20%).

TABLE 14

Effect on the progress of Listeria monocytogene infection in mice

| | Progress after secondary infection | |
|---|---|---|
| Experimental group | Mortality | % of surviving animals with organisms in the liver |
| Control Group (untreated) | 4/10 | 100 |
| Active product group (compound of Example 34; 4 × 10 mg/kg i.p.) | 0/10 | 20 |

Accordingly, the test substance confers distinct protection from the fatal consequences of secondary infection.

9. Effect on Staphylococcus aureus infection of immuno-suppressed mice

It is known that distinct immunosuppression can be induced in experimental animals by multiple administration of a cytostatic and is expressed by an increased susceptibility to infection with a drastic rise in mortality. The investigation was now of whether the mortality rate can be effectively lowered by treatment with the compounds the formula I. For this purpose, female B6D2F1 mice were treated intravenously on three consecutive days with 7.5 mg/kg adriamycin (ADM) each day, and infected on day 5 with $2 \times 10^6$ organisms of the bacterium Staphylococcus aureus, and the mortality was determined up to day 45 of the experiment (positive control). Another group of infected animals which had not, however, been immunosuppressed by pretreatment with ADM was included as negative control. The immunosuppressed animals in the three active product groups received, on 4 consecutive days starting one day before the infection, the test substance, with intraperitoneal doses each of 0.1, 1 or 10 mg/kg being administered. Each experimental group comprised 20 animals.

The test results shown in Table 15 demonstrate that the mortality in the positive control animals with ADM-induced immunodeficiency drastically increased compared with that of the negative control with intact immune defenses, and that treatment with the test substance results in a distinct lowering of the mortality rate among the immunosuppressed animals.

TABLE 15

Effect on Staphylococcus aureus infection of immunosuppressed mice

| Experimental group | Dose in mg/kg (4 × i.p.) | Mortality |
|---|---|---|
| Negative control | | 0/20 |
| Positive control | | 13/20 |
| Active product groups | 0.1 | 5/20 |
| (with compound from | 1.0 | 8/20 |
| Example 34) | 10.0 | 8/20 |

10. Effect on the antibody response of the mouse to dead Escherichia (E.) coli organisms and tetanus toxoid Groups each containing 5 female NMRI mice with a body weight of 18 to 20 g were formed, and each of the animals received either intravenous administration of $10^8$ heat-killed E coli bacteria or 300 Lf (limes of flocculation) of tetanus toxoid. Oral administration of the test substance in physiological saline (PBS) in doses of 5, 10, 20, 40 or 80 mg/kg, or of the pure vehicle (control groups), was carried out at the same time as administration of the antigen. After 10 and 20 days, blood was taken from the retroorbital venous plexus of the mice and, in the sera obtained therefrom, the IgG and IgM antibodies against E. coli organisms and tetanus toxoid were determined with the aid of the ELISA technique known to those skilled in the art, using homologous lipopolysaccharide from E. coli and tetanus toxoid, respectively, as antigen. The magnitude of the extinctions measured in the photometer is a measure of the amount of antibodies formed. The results are compiled in Table 16. According to this, the antibody response to both antigens is significantly raised after oral treatment with the test substance compared with that of the untreated animals.

TABLE 16

Stimulation of the antibody response of the mouse to dead E. coli organisms and tetanus toxoid

| | | Antibody response ($mE_{492nm}$-ELISA) to | | |
|---|---|---|---|---|
| Test substance | Dose in mg/kg (1 × p.o.) | Dead E. coli organisms | | Tetanus toxoid |
| | | IgM* | IgG** | IgG** |
| PBS (vehicle) | | 925 ± 118 | 1115 ± 141 | 566 ± 270 |
| Compound from Example 34 | 5 | 1217 ± 264 | 1377 ± 324 | 865 ± 182 |
| | 10 | 1411 ± 179 | 1663 ± 191 | 1213 ± 255 |
| | 20 | 1657 ± 231 | 1951 ± 468 | 1852 ± 261 |
| | 40 | 1523 ± 288 | 2434 ± 312 | 1357 ± 348 |
| | 80 | 1459 ± 208 | 2217 ± 273 | 1154 ± 232 |

*10-day value
**20-day value

11. Effect on chronic Salmonella typhimurium infection in the mouse

Female NMRI mice (20 animals/group) were infected by intravenous administration of $5 \times 10^3$ Salmonella typhimurium organisms. The animals subsequently developed a chronic infection which was characterized by persistent bacterial colonization of the organs, such as the liver and the spleen, with necrosis. The test substance was administered intraperitoneally in a dose of 5 mg/kg at intervals of two days from day 3 to day 21 after infection. The animals in a control group received only the vehicle. On day 22 after the infection, the mortality in both experimental groups was determined, and the organs of the animals which survived were examined for organisms and necrosis. The data in Table 17 show that the mortality, the number of animals with organism-positive livers and the frequency of liver and spleen necroses are lowered in the animals treated with the test substance compared with the untreated animals in the control group.

TABLE 17

Effect on the progress of chronic Salmonella typhimurium infection in mice

| | | % of surviving animals with | | | |
|---|---|---|---|---|---|
| Experimental group | Mortality | Organism-positive livers | Liver necroses | Severe liver necroses | Spleen necroses |
| Control | 14/20 | 83 | 83 | 67 | 17 |
| Product group* | 8/20 | 67 | 58 | 42 | 0 |

*Treated with the compound of Example 34 (10 × 5 mg/kg i.p.)

12. Stimulation of defenses against B16 melanoma in the mouse

A primary tumor was generated with $2 \times 10^5$ live B16 melanoma cells in female C57B1/6 mice with a body weight of 18 to 20 g and, after having grown to a diameter of 0.65 cm, was removed surgically. The animals subsequently died of metastases in the lung. The investigation now was of whether the mean survival time after removal of the primary tumor, that is to say the time at which 50% of the animals are still alive, can prolonged by intraperitoneal treatment with the compounds of the formula I. For this purpose, after amputation of the primary tumor, the mice were divided into groups each containing 10 animals and were treated with i.p. doses each of 1.25 or 2.5 mg/kg test substance at intervals of 2 days from day 4 to day 100. The animals in the control group received merely the pure vehicle PBS (physiological saline) in the same therapeutic regimen. The experimental results are reproduced in Table 18. According to this, 50% of the animals in the control group had died after 22 days, whereas the mice treated with the test substance showed a significant prolongation of the mean survival time to 41 and 43 days, respectively.

TABLE 18

Stimulation of the defenses against B16 melanoma

| Test substance | Dose in mg/kg i.p. | % survival after 100 days | Mean survival time in days |
|---|---|---|---|
| PBS (vehicle) | | 0 | 22 |
| Compound of Example 34 | 1.25 | 20 | 41 |
| | 2.50 | 30 | 43 |

We claim:

1. A compound of the formula I, and/or one of its physiologically tolerated salts where appropriate,

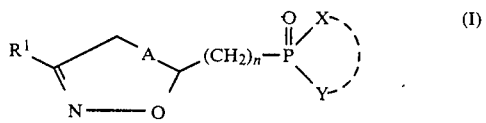

where
$R^1$ represents
(a) a straight-chain or branched alkyl or alkenyl group which has 1 to 6 carbon atoms and whose carbon chain can be substituted by halogen, hydroxyl, ($C_1$-$C_4$)alkoxy, ($C_1$-$C_4$)acyloxy or aryl which is optionally substituted by ($C_1$-$C_4$)alkoxy or halogen, or
(b) a mono- or binuclear aromatic or heteroaromatic group having 1 or 2 nitrogen atoms and/or one sulfur or oxygen atom in the ring system, it being possible for this group to be substituted one or more times and identically or differently by straight-chain or branched ($C_1$-$C_4$)alkyl, ($C_3$-$C_6$)cycloalkyl, hydroxyl, ($C_1$-$C_3$)alkoxy, unsubstituted phenoxy, ($C_1$-$C_4$)acyloxy or benzoyloxy, halogen, trifluoromethyl, nitro, optionally mono- or disubstituted amino, ($C_1$-$C_4$)alkoxycarbonyl, carboxyl, carbamoyl, ($C_1$-$C_4$)alkylcarbonyl, whose carbonyl group can in each case also be in ketalized form, or benzyl or phenyl which is optionally ring-substituted by ($C_1$-$C_4$)alkyl, halogen or ($C_1$-$C_3$)alkoxy, or
(c) carboxyl or alkoxycarbonyl having 1 to 4 carbon atoms in the alkyl moiety or
(d) arylcarbonyl which is optionally substituted in the aryl moiety by ($C_1$-$C_4$)alkyl, halogen or ($C_1$-$C_3$)alkoxy, or
(e) halogen, A denotes a C,C single bond or a C,C double bond,
n denotes an integer from 0 to 2, and
X and Y, which can be identical or different, each denote, independently of one another, a straight-chain or branched ($C_1$-$C_4$)alkyl group, the radical —$OR^2$ or the group —$NR^2R^3$, where $R^2$ and $R^3$ represent hydrogen or optionally substituted ($C_1$-$C_6$)alkyl radicals which, in the group —$NR^2R^3$, can also form together with the nitrogen atom a five- to seven-membered ring or, in the structural element —P(O)($OR^2$)$_2$, can form together with the phosphorus atom a heterocycle of the formula

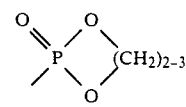

which is optionally also substituted by ($C_1$-$C_3$)alkyl, ($C_1$-$C_4$)alkoxycarbonyl or carboxyl, and where the compounds of the formula I can, where appropriate, be in the form of pure stereoisomers or mixtures thereof, excepting the compounds 3-phenyl-2-isoxazolin-5-ylphosphonic acid, 3-methyl(and phenyl)-2-isoxazolin-5-ylphosphonate, dipropyl 3-(3-nitrophenyl)-2-isoxazolin-5-ylphosphonate, 3-methyl(and phenyl)-2-isoxazollin-5-ylphosphonic tetramethyldiamide, 3-phenyl-2-isoxazolin-5-ylmethylphosphonic acid and the diethyl ester thereof, diethyl 3-methyl(ethyl, isopropyl, tert.butyl, methoxymethyl, phenyl and ethoxycarbonyl)-5-isoxazolylmethylphosphonate, 3-(4-fluoro- and 4-chlorophenyl)-5-isoxazolyl(P-methyl)-phosphinic acid and methyl 3-phenyl-5-isoxazolyl(P-methyl)phosphinate, where the racemic forms are being dealt with where appropriate.

2. A compound of the formula I as claimed in claim 1, its stereoisomeric forms where appropriate and its salts where appropriate, wherein
$R^1$ represents
(a) optionally branched ($C_1$-$C_4$)alkyl or ($C_1$-$C_4$)hydroxyalkyl or phenyl($C_1$-$C_2$)alkyl or phenyl($C_2$-$C_3$)alkenyl,
(b) phenyl, naphthyl, pyridyl or thienyl, each of which is unsubstituted or substituted one or more times by ($C_1$-$C_4$) alkyl, hydroxyl, ($C_1$-$C_2$)alkoxy, phenoxy, halogen, trifluoromethyl, nitro, di($C_1$-$C_2$)alkylamino, ($C_1$-$C_2$)alkoxycarbonyl, carboxyl or phenyl
(c) carboxyl or meth- or ethoxycarbonyl,
(d) benzoyl,
(e) chlorine or bromine,
A denotes a C,C single bond or a C,C double bond,
n represents 0 or 1, and
X and Y, which can be identical or different, represent independently of one another a methyl or ethyl group or the radicals —$OR^2$ or —$NR^2R^3$, where $R^2$ represents hydrogen, methyl or ethyl, and $R^3$ likewise represents hydrogen, methyl or ethyl, or else represent the carbon skeleton of an optionally carboxyl-protected amino acid, the radicals $R^2$ and $R^3$ in the group —$NR^2R^3$ can also form together with the nitrogen atom a pyrrolidine, piperidine or morpholine ring, and the radicals —$OR^2$ in the structural element —$P(O)(OR^2)_2$ can form together with the phosphorus atom a 2-oxo-1,3,2-dioxaphospholane or 2-oxo-1,3,2-dioxaphosphorinane ring, each of which is optionally substituted by $(C_1-C_2)$alkyl, and where these compounds can, where appropriate, be in the form of pure stereoisomers or mixtures thereof.

3. A compound of the formula I as claimed in claim 1, its stereoisomeric forms where appropriate and its salts where appropriate, in which $R^1$ represents tert.butyl, benzyl, phenyl, naphthyl, pyridyl or thienyl, or phenyl which is substituted by methyl, hydroxyl, methoxy, phenoxy, chlorine, fluorine, trifluoromethyl, nitro, dimethylamino, methoxycarbonyl or carboxyl, A denotes a C,C single bond or a C,C double bond, n represents 0 or 1, or X and Y denote, independently or one another, hydroxyl, methoxy or ethoxy, or X denotes methyl and Y denotes hydroxyl, methoxy or ethoxy, and where these compounds can, where appropriate, be in the form of pure stereoisomers or mixtures thereof.

4. A compound of the formula I as claimed in claim 3, its stereoisomeric forms and its salts where appropriate, wherein A represents a C,C single bond, and n has the value 0, and where the racemic forms thereof are being dealt with where appropriate.

5. A compound of the formula I as claimed in claim 1, its stereoisomeric forms and its salts, in which $R^1$ represents tert.butyl or phenyl, X and Y each denote hydroxyl, or X denotes methyl and Y denotes hydroxyl, A represents a C,C single bond, and n has the value 0, where these compounds can be in the form of pure stereoisomers or mixtures thereof.

6. A compound of the formula I as claimed in claim 1, its stereoisomeric forms and its salts, which represents 3-phenyl- or 3-tert.butyl-2-isoxazolin-5-yl(P-methyl)-phosphinic acid.

7. A compound of the formula I as claimed in claim 1 and its salts, which represents an enantiomeric form of 3-phenyl-2-isoxazolin-5-ylphosphonic acid.

8. A method of treating a person for protecting said person from diseases of the immune system, which comprises administering to said person an effective amount of at least one compound of the formula I, its stereoisomeric forms where appropriate or its physiologically tolerated salts where appropriate,

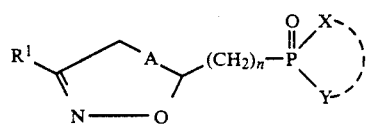

where
$R^1$ represents
(a) a straight-chain or branched alkyl or alkenyl group which has 1 to 6 carbon atoms and whose carbon chain can be substituted by halogen, hydroxyl, $(C_1-C_4)$alkoxy, $(C_1-C_4)$acyloxy or aryl which is optionally substituted by $(C_1-C_4)$alkoxy or halogen, or
(b) a mono- or binuclear aromatic or heteroaromatic group having 1 or 2 nitrogen atoms and/or one sulfur or oxygen atom in the ring system, it is being possible for this group to be substituted one or more times and identically or differently by straight-chain or branched $(C_1-C_4)$alkyl, $(C_3-C_6$-)cycloalkyl, hydroxyl, $(C_1-C_3)$alkoxy, unsubstituted phenyl, $(C_1-C_4)$acyloxy or benzoyloxy, halogen, trifluoromethyl, nitro, optionally mono- or disubstituted amino, $(C_1-C_4)$alkylcarbonyl, carboxyl, carbamoyl, $(C_1-C_4)$alkylcarbonyl, whose carbonyl group can in each case also be in ketalized form, or benzyl or phenyl which is optionally ring-substituted by $(C_1-C_4)$-alkyl, halogen or $(C_1-C_3)$alkoxy, or (c) carboxyl or alkoxycarbonyl having 1 to 4 carbon atoms in the alkyl moiety or (d) arylcarbonyl which is optionally substituted in the aryl moiety by $(C_1-C_4)$alkyl, halogen or $(C_1-C_3)$alkoxy, or (e) halogen, A denotes a C,C single bond or a C,C double bond, n denotes an integer from 0 to 2, and X and Y, which can be identical or different, each denote, independently of one another, a straight-chain or branched $(C_1-C_4)$alkyl group, the radical —$OR^2$ or the group —$NR^2R^3$, where $R^2$ and $R^3$ represent hydrogen or optionally substituted $(C_1-C_6)$ alkyl radicals which, in the group —$NR^2R^3$, can also form together with the nitrogen atom a five- to seven-membered ring or, in the structural element, —$P(O)(OR^2)_2$, can form together with the phosphorus atom a heterocycle of the formula

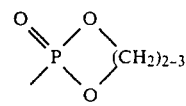

which is optionally also substituted by $(C_1-C_3)$alkyl, $(C_1-C_4)$alkoxycarbonyl or carboxyl, and where the compounds of the formula I can, where appropriate, be in the form of pure stereoisomers or mixtures thereof, excepting the compounds 3-phenyl-2-isoxazolin-5-ylphosphonic acid, 3-methyl(and phenyl)-2-isoxazolin-5-ylphosphonate, dipropyl 3-(3-nitrophenyl)-2-isoxazolin-5-ylphosphonate, 3-methyl(and phenyl)-2-isoxazollin-5-ylphosphonic tetramethyldiamide, 3-phenyl-2-isoxazolin-5-ylmethylphosphonic acid and the diethyl ester thereof, diethyl 3-methyl(ethyl,isopropyl, tert.butyl, methoxymethyl, phenyl and ethoxycarbonyl)-5-isoxazolylmethylphosphonate, 3-(4-fluoro- and 4-chlorophenyl)-5-isoxazolyl(P-methyl)-phosphinic acid and methyl 3-phenyl-5-isoxazolyl(P-methyl)phosphinate.

9. A method of treating a person for protecting said person from disease of the immune system, which comprises administering to said person a pharmaceutical composition comprising a pharmaceutically suitable carrier and an effect amount of at least one compound of the formula I, and/or one of its physiologically tolerated salts where appropriate,

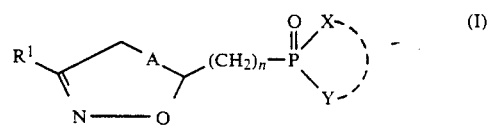

where
$R^1$ represents
(a) a straight-chain or branched alkyl or alkenyl group which has 1 to 6 carbon atoms and whose carbon chain can be substituted by halogen, hydroxyl, ($C_1$–$C_4$)alkoxy, ($C_1$–$C_4$)acyloxy or aryl which is $C_1$ optionally substituted by ($C_1$–$C_4$)alkoxy or halogen, or (b) a mono- or binuclear aromatic or heteroaromatic group having 1 or 2 nitrogen atoms and/or one sulfur or oxygen atom in the ring system, it being possible for this group different to be substituted one or more times and identically or differently by straight-chain or branched ($C_1$–$C_4$)alkyl, ($C_3$–$C_6$)cycloalkyl, hydroxyl, ($C_1$–$C_3$)alkoxy, unsubstituted phenoxy, ($C_1$–$C_4$)acyloxy or benzoyloxy, halogen, trifluoromethyl, nitro, optionally mono- or disubstituted amino, ($C_1$–$C_4$)-alkoxycarbonyl, carboxyl, carbomoyl ($C_1$–$C_4$)alkylcarbonyl, whose carbonyl group can in each case also be in ketalized form, or benzyl or phenyl which is optionally ring-substituted by ($C_1$–$C_4$)alkyl, halogen or ($C_1$–$C_3$)alkoxy, or (c) carboxyl or alkoxycarbonyl having 1 to 4 carbon atoms in the alkyl moiety or (d) arylcarbonyl which is optionally substituted in the aryl moiety by ($C_1$–$C_4$)alkyl, halogen or ($C_1$–$C_3$)alkoxy, or (e) halogen A denotes a C,C single bond or a C,C double bond,
n denotes an integer from 0 to 2, and
X and Y, which can be identical or different, each denote, independently of one another, a straight-chain or branched ($C_1$–$C_4$)alkyl group, the radical —$OR^2$ or the group —$NR^2R^3$, where $R^2$ and $R^3$ represent hydrogen or optionally substituted ($C_1$–$C_6$)alkyl radicals which, in group —$NR^2R^3$, can also form together with the nitrogen atom a five- to seven-membered ring or, in the structural element —P(O)-($OR^2$)$_2$, can form together with the phosphorus atom a heterocycle of the formula

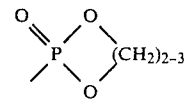

which is optionally also substituted by ($C_1$–$C_3$)alkyl, ($C_1$–$C_4$)alkoxycarbonyl or carboxyl, and where the compounds of the formula I can, where appropriate, be in the form of pure stereoisomers or mixtures thereof.

10. A method as claimed in claim 8 for protecting from and/or curing tumors, infections and/or autoimmune diseases and for providing adjuvants for vaccines.

11. A method as claimed in claim 9 for protecting from and/or curing tumors, infections and/or autoimmune diseases and for providing adjuvants for vaccines.

* * * * *